(12) United States Patent
Okada

(10) Patent No.: US 7,582,054 B2
(45) Date of Patent: Sep. 1, 2009

(54) ENDOSCOPE TREATMENT TOOL INSERTION-EXTRACTION SYSTEM

(75) Inventor: Tsutomu Okada, Tokyo (JP)

(73) Assignee: Olympus Corporation, Tokyo (JP)

( * ) Notice: Subject to any disclaimer, the term of this patent is extended or adjusted under 35 U.S.C. 154(b) by 656 days.

(21) Appl. No.: 10/986,125

(22) Filed: Nov. 10, 2004

(65) Prior Publication Data

US 2005/0119522 A1    Jun. 2, 2005

(30) Foreign Application Priority Data

Nov. 28, 2003   (JP)   ............... 2003-398831

(51) Int. Cl.
    *A61B 1/00*   (2006.01)
(52) U.S. Cl. ...................... 600/106; 600/104
(58) Field of Classification Search ................. 600/104, 600/106, 107, 114, 130, 1, 113
    See application file for complete search history.

(56) References Cited

U.S. PATENT DOCUMENTS

| | | | | |
|---|---|---|---|---|
| 2,711,734 A * | 6/1955 | Moe | ............. | 604/171 |
| 3,835,854 A * | 9/1974 | Jewett | ............. | 604/159 |
| 5,346,498 A * | 9/1994 | Greelis et al. | ............. | 606/108 |
| 5,376,094 A * | 12/1994 | Kline | ............. | 606/113 |
| 5,431,645 A * | 7/1995 | Smith et al. | ............. | 606/1 |
| 5,540,649 A * | 7/1996 | Bonnell et al. | ............. | 600/114 |
| 5,695,491 A * | 12/1997 | Silverstein | ............. | 606/1 |
| 5,779,623 A * | 7/1998 | Bonnell | ............. | 600/114 |
| 5,882,294 A * | 3/1999 | Storz et al. | ............. | 600/114 |
| 5,931,833 A * | 8/1999 | Silverstein | ............. | 606/1 |
| 6,074,402 A * | 6/2000 | Peifer et al. | ............. | 606/139 |
| 6,171,234 B1 * | 1/2001 | White et al. | ............. | 600/102 |
| 6,358,199 B1 * | 3/2002 | Pauker et al. | ............. | 600/114 |
| 6,569,084 B1 * | 5/2003 | Mizuno et al. | ............. | 600/102 |
| 6,626,824 B2 * | 9/2003 | Ruegg et al. | ............. | 600/104 |
| 6,726,675 B1 * | 4/2004 | Beyar | ............. | 604/510 |
| 7,118,582 B1 * | 10/2006 | Wang et al. | ............. | 606/139 |
| 7,179,223 B2 * | 2/2007 | Motoki et al. | ............. | 600/131 |
| 2003/0176770 A1 * | 9/2003 | Merril et al. | ............. | 600/118 |
| 2005/0041889 A1 * | 2/2005 | Scarberry | ............. | 383/37 |
| 2006/0287574 A1 * | 12/2006 | Chin | ............. | 600/114 |

FOREIGN PATENT DOCUMENTS

| | | |
|---|---|---|
| JP | S57-117823 | 7/1982 |
| JP | 2000-000207 | 1/2000 |

* cited by examiner

*Primary Examiner*—John P Leubecker
*Assistant Examiner*—Victoria W Chen
(74) *Attorney, Agent, or Firm*—Scully, Scott, Murphy & Presser, P.C.

(57) ABSTRACT

An endoscope treatment tool insertion-extraction system is provided with an endoscope having a forceps channel, and a treatment tool unit having a treatment tool that can be inserted and extracted through the forceps channel; and the treatment tool unit is provided with an insertion-extraction mechanism which carries out feeding into or drawing out of the treatment tool through the forceps channel, and a driving section that drives this insertion-extraction mechanism.

24 Claims, 23 Drawing Sheets

*FIG.3*
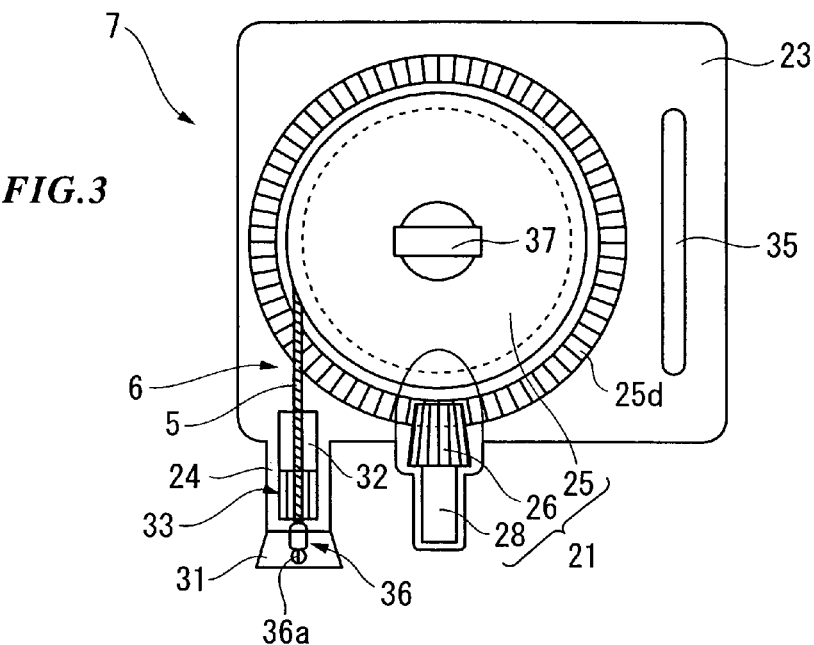
*FIG.4A* *FIG.4B*
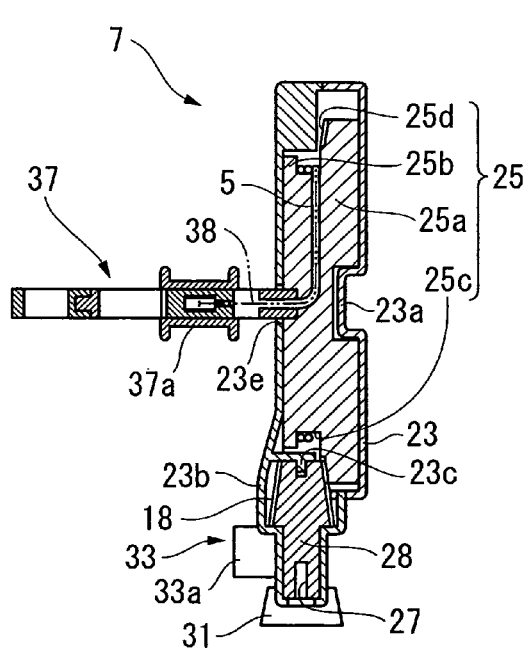 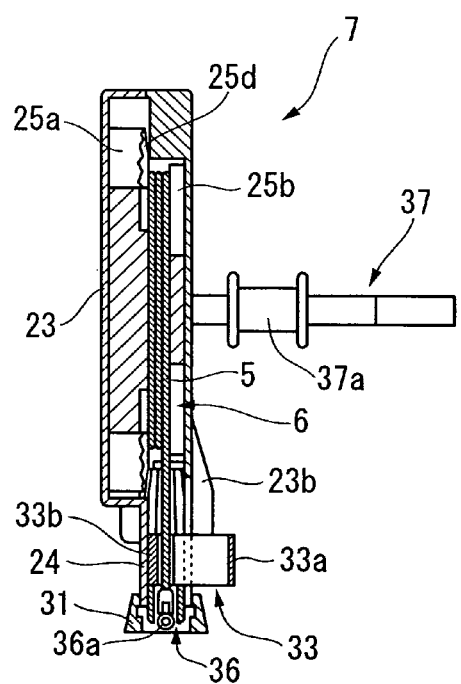

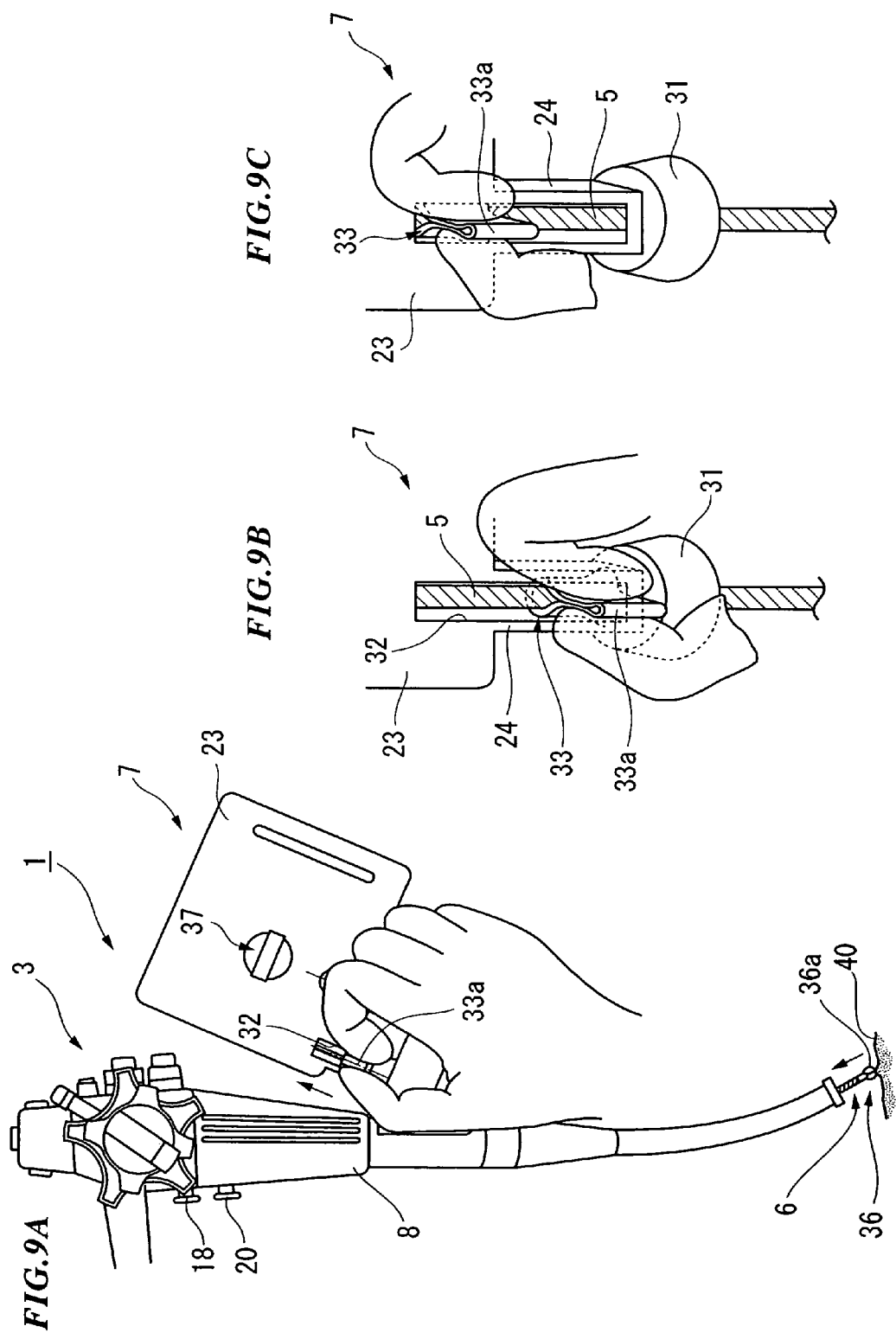

ENDOSCOPE TREATMENT TOOL INSERTION-EXTRACTION SYSTEM

BACKGROUND OF THE INVENTION

Priority is claimed on Japanese Patent Application No. 2003-398831, filed on Nov. 28, 2003, the content of which is incorporated herein by reference.

1, Field of the Invention

The present invention relates to an endoscope treatment tool insertion-extraction system for automatically inserting and extracting a treatment tool, such as a forceps, a catheter or a high frequency knife, that is inserted into a body cavity through a forceps channel of an endoscope.

2, Description of Related Art

Conventionally, when a treatment tool such as a forceps is inserted into a body cavity through a forceps channel of an endoscope, an operator inserts it into the forceps channel while holding the treatment tool in their own hand. For example, since the total length of an endoscope for use with the colon can be as long as 2 m, an endoscope provided with an insertion-extraction apparatus that inserts and extracts a treatment tool that is inserted from the treatment tool insertion opening of the endoscope has been proposed, in order to reduce the labor of the treatment tool insertion operation (for example, refer to FIG. 1 of Japanese Unexamined Patent Application, First Publication No. S57-117823).

Moreover, an insertion-extraction apparatus that houses and retains a plurality of treatment tools in individual housing sections has also been proposed (for example, refer to FIG. 1, FIG. 3, FIG. 6 and FIG. 7 of Japanese Unexamined Patent Application, First Publication No. 2000-207). This insertion-extraction apparatus is provided with an insertion-extraction device that inserts and extracts any of each of the treatment tools held in the housing sections, to and from the forceps channel of the endoscope, and an operating device for a treatment section arranged at the tip end of the treatment tool.

SUMMARY OF THE INVENTION

An endoscope treatment tool insertion-extraction system of the present invention is provided with: an endoscope having a forceps channel, and a treatment tool unit having a treatment tool that can be inserted and extracted through the forceps channel; and the treatment tool unit is provided with an insertion-extraction mechanism which carries out feeding into or drawing out of the treatment tool through the forceps channel, and a driving section that drives this insertion-extraction mechanism.

The insertion-extraction mechanism may be provided with a rotation member that winds the treatment tool, and a conversion mechanism that converts a driving force of the driving section into a rotation force of the rotation member.

The treatment tool unit may be provided with a manual operating section whereby part of the treatment tool is manually moved forward and backward.

Teeth may be formed on the circumference of the rotation member, and the conversion device may be a gear that meshes with the teeth.

A power source of the driving section may be built into a light source apparatus of the endoscope.

A power source of the driving section may be built into an operating section of the endoscope.

An operating section of the treatment tool may be provided on a rotation axis of the rotation member.

An operating section of the treatment tool may be built into the rotation member, so that it can be taken out from this rotation member.

The manual operating section may be provided with a grip part that manually grips the treatment tool.

A finger hole to hold this treatment tool unit by hand may be provided in the treatment tool unit.

The forceps channels and the treatment tool units may be provided as two of each.

At least the part of the insertion section of the treatment tool that is wound onto the rotation member may be constructed of two overlapped plate shaped members, and at least one of these plate shaped members may have a folding groove provided in the widthwise center along its lengthwise direction, and be folded so that the folding groove faces outwards.

The treatment tool and the insertion-extraction mechanism may be provided as two each in the treatment tool unit.

In this case, rotation members onto which each of the treatment tools is wound may be provided for each of the insertion-extraction mechanisms, and these rotation members may be connectable to the driving section.

In this case, a selection section may be provided, which selects either of the two insertion-extraction mechanisms and connects it to the driving section.

Moreover, each of the rotation members may be disposed coaxially, and teeth which mesh with the driving section while opposing to each other, may be provided on each circumference of these rotation members, and the two insertion sections may be respectively wound in opposite directions, onto the rotation members.

The treatment tool unit may be packaged in a sterile condition.

The treatment tool unit may be provided with a property of resistance to chemicals for disinfection and sterilization and to high pressure steam sterilization.

A part that projects from the rotation member of the insertion section of the treatment tool may move forward and backward along a direction tangential to the rotation member.

The driving section may be provided with a motor.

BRIEF DESCRIPTION OF THE DRAWINGS

FIG. 3 is a side view of the same treatment tool unit, with some parts in cross section.

FIG. 4A and FIG. 4B are cross sectional views along the line A-A and the line B-B of FIG. 2C respectively.

FIG. 9A to FIG. 9C are diagrams to describe the operation method of the same endoscope treatment tool insertion-extraction unit.

DETAILED DESCRIPTION OF THE INVENTION

Figure 1:
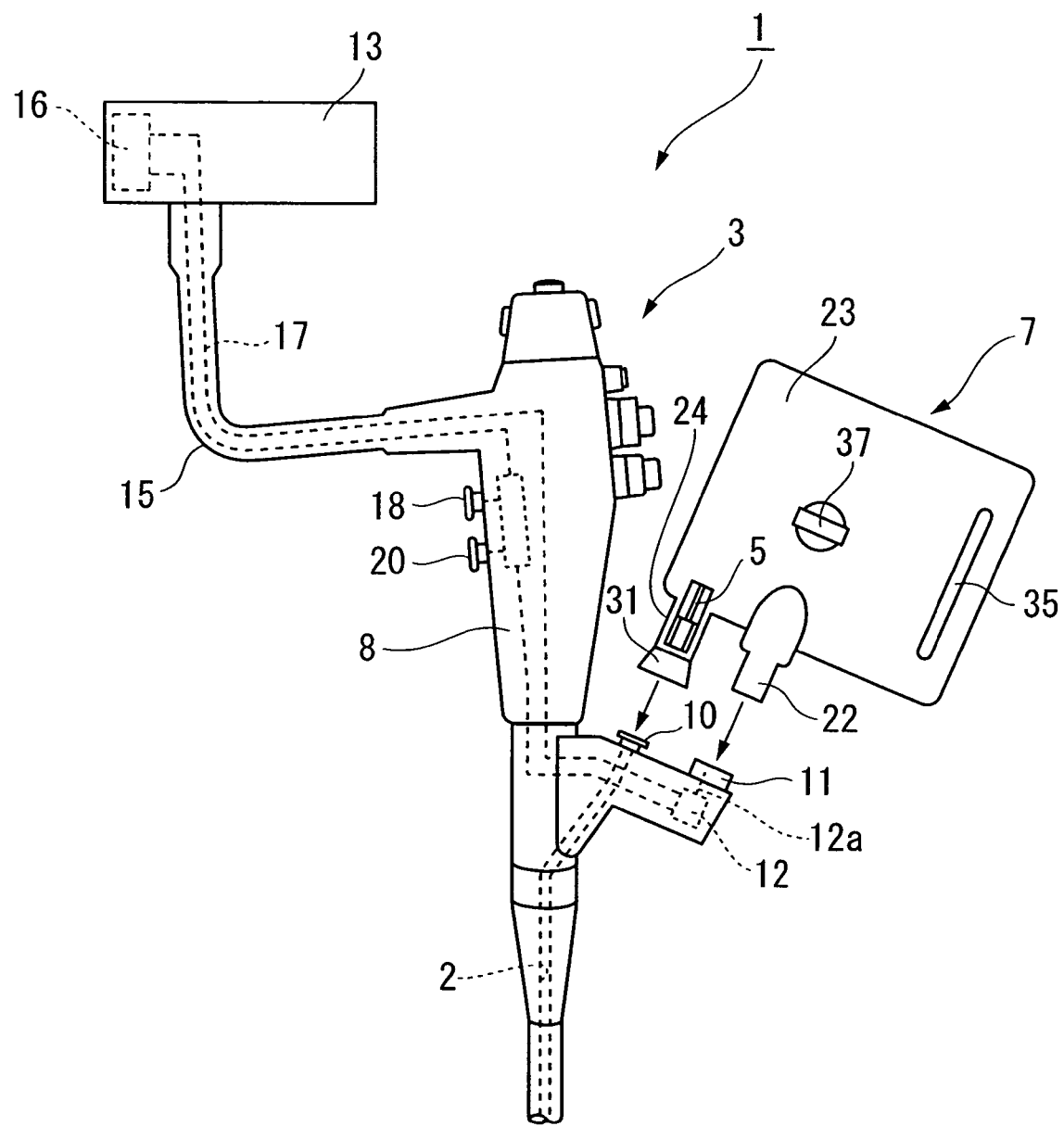
FIG. 1 is a side view showing an entire endoscope treatment tool insertion-extraction system according to a first embodiment of the present invention.
Figure 2:
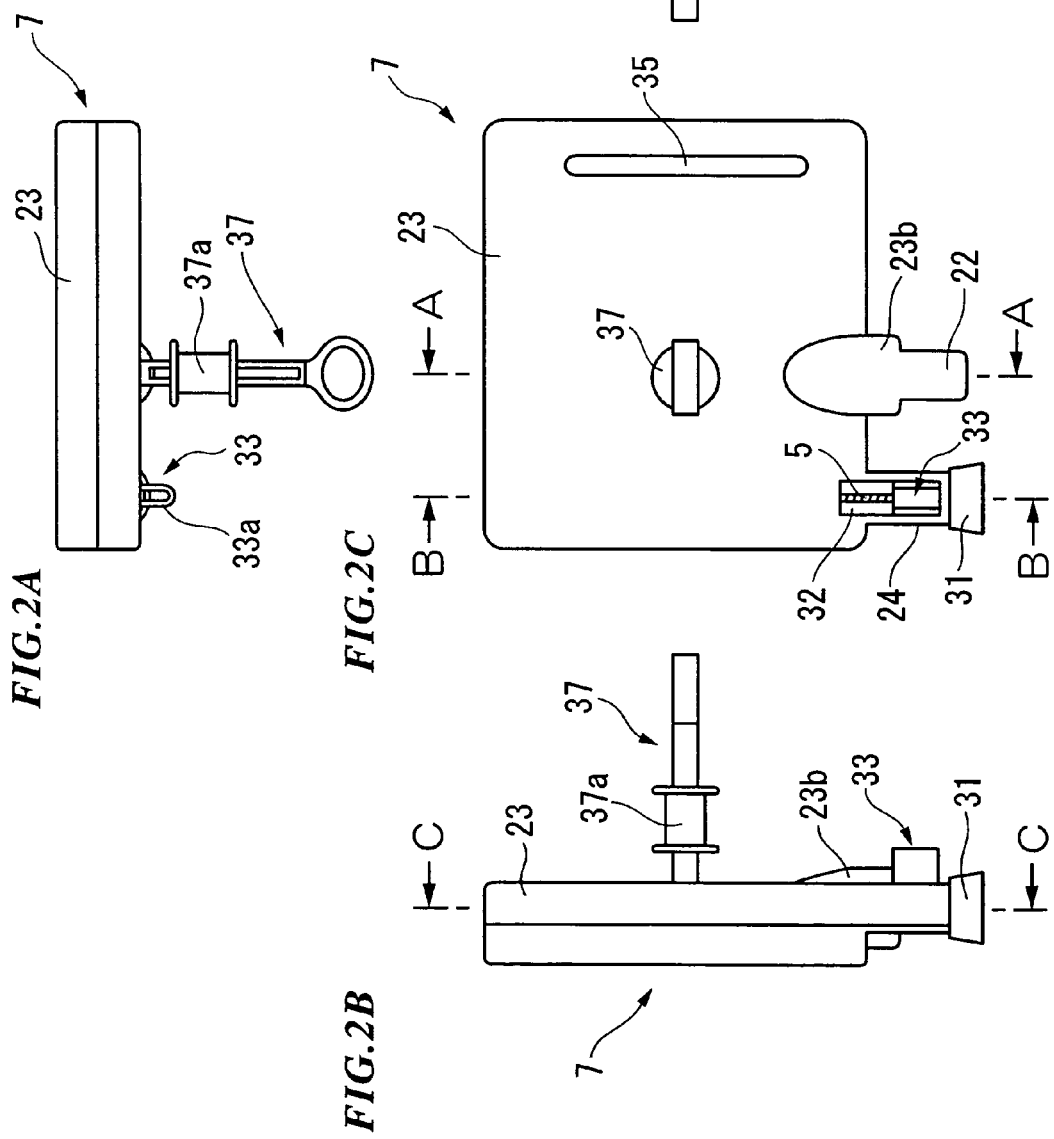
FIG. 2A to FIG. 2D are views of a treatment tool unit of the same embodiment when seen from four directions.
Figure 5:
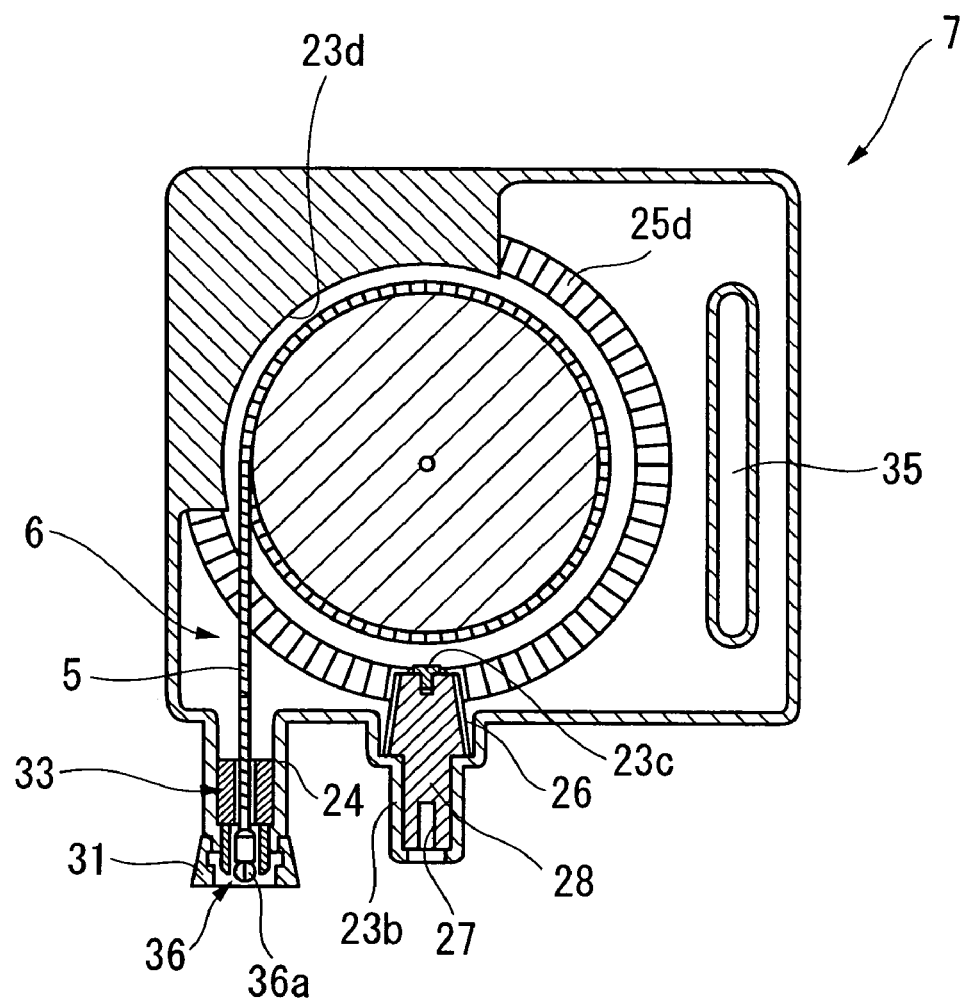
FIG. 5 is a sectional side view of the same treatment tool unit.

A first embodiment of an endoscope treatment tool insertion-extraction system of the present invention is described with reference to FIG. 1 to FIG. 11.

An endoscope treatment tool insertion-extraction system 1 of the present embodiment is provided with an endoscope 3 having a forceps channel 2, and a treatment tool unit 7 that has biopsy forceps (treatment tool) 6 that includes an insertion section 5 that can be inserted and extracted through the forceps channel 2.

As shown in FIG. 1, the endoscope 3 is provided with an operating section 8. The operating section 8 is provided with a forceps opening 10 that links to the forceps channel 2, a connection section 11 that is disposed near the forceps opening 10 and can engage with the treatment tool unit 7, and a motor (driving section) 12 that is built in near the connection section 11 and supplies power to the treatment tool unit 7. A motor rotation shaft 12a of the motor 12 is exposed in the connection section 11.

The operating section 8 is connected to a light source apparatus 13 that supplies light to the endoscope 3 via a universal cord 15. The motor 12 is connected to a motor drive power source 16 provided in the light source apparatus 13 via a wiring 17 in the universal cord 15.

Also, the operating section 8 is, for example, provided with a first switch 18 that rotates clockwise or stops the motor 12, and a second switch 20 that rotates counterclockwise or stops the motor 12. These switches 18 and 20 turn ON when pressed, and rotate the motor 12 in the clockwise rotation direction or counterclockwise rotation direction, and stop the motor 12 when released.

The treatment tool unit 7 is provided with an insertion-extraction mechanism 21 that is capable of feeding the biopsy forceps 6 into the forceps channel 2 and drawing back the biopsy forceps 6 from the forceps channel 2, and a square shaped cassette 23 which houses an insertion-extraction mechanism 21, and on which is formed a motor connection section 22 which can engage with the connection section 11.

The cassette 23 is provided with a treatment tool guiding section 24, which is formed integrally with the cassette 23 in a tubular shape, and which guides the biopsy forceps 6 to the forceps opening 10.

The insertion-extraction mechanism 21, as shown in FIG. 2A to FIG. 5, is provided with: a bobbin (rotation member) 25 which is capable of winding the insertion section 5 of the biopsy forceps 6; a gear (conversion mechanism) 26 that is connected to the motor 12 and that converts a driving force of the motor 12 into a rotation force of the bobbin 25 by transmitting this driving force to the bobbin 25; and a rod shaped engagement part 28 at the bottom end of which is formed an engagement hole 27 that can be connected to the rotation shaft 12a of the motor 12.

The bobbin 25 is rotatably supported on a protrusion 23a that projects towards the inside of the cassette 23.

The bobbin 25 is provided with: a larger outer diameter section 25a provided on one side; a smaller outer diameter section 25b provided on the other side; and a winding section 25c, which is provided between the larger outer diameter section 25a and the smaller outer diameter section 25b, and which has an outer diameter still smaller than that of the smaller outer diameter section 25b.

Teeth 25d formed in a serrated shaped are formed on the side face of the larger outer diameter section 25a around the entire circumference. The gear 26 is meshed with the teeth 25d.

The gear 26 is housed in a gear housing section 23b formed integrally with the cassette 23. This gear 26 is pivoted on a projection 23c integrally formed inside the cassette 23 so as to project towards the inside, and is connected to the upper end of the motor connection section 22.

The tip end side of the insertion section 5 of the biopsy forceps 6 is wound around the winding section 25c so as to extend in a direction tangential to the bobbin 25 and be guided into the treatment tool guiding section 24.

A forceps opening connection member 31 formed from elastic material, such as rubber, is provided at the end of the treatment tool guiding section 24. A window 32 that extends in the axial direction of the treatment tool guiding section 24 is formed in the central part of the treatment tool guiding section 24.

Figure 6A:
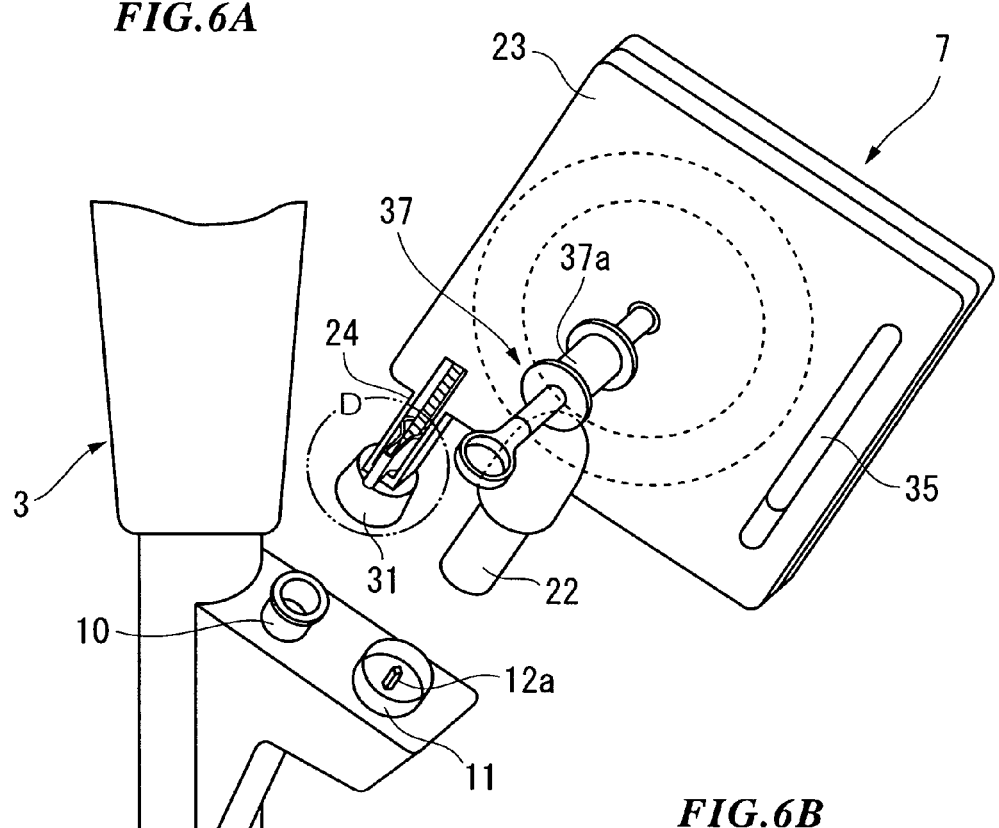
FIG. 6A and FIG. 6B are perspective views showing the same treatment tool unit in a state of being attached to an endoscope.
Figure 6B:
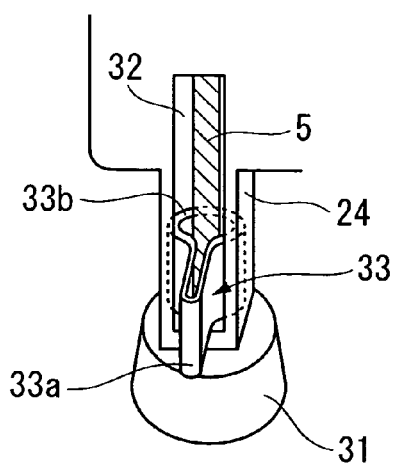

As shown in FIG. 6B, a holding section (manual operating section) 33 that can control the forward and backward movement of the middle section of the insertion section 5 of the biopsy forceps 6 guided from the bobbin 25 into the treatment tool guiding section 24, is provided in the window 32. The holding section 33 is constructed as an annular shaped elastic member, and a part that is housed inside the treatment tool guiding section 24 constitutes a pipe shaped section 33b. Usually, the holding section 33 encloses the periphery of part of the insertion section 5 lengthwise, allowing the insertion section 5 to move. Also, a knob 33a is formed on a part of the holding section 33 which projects outward from the window 32. Therefore, since the diameter of the pipe shaped section 33b reduces and holds the insertion section 5 when the knob 33a is gripped and squeezed, the insertion section 5 can be moved manually.

Moreover, a constraining section 23d (refer to FIG. 5) that prevents deviation of the insertion section 5 of the biopsy forceps 6, is provided in the cassette 23 along a part of the circumference faces of the smaller outer diameter section 25b and the winding section 25c, Furthermore, a finger hole 35 that can be gripped with a finger is formed on the outside surface of the cassette 23.

The biopsy forceps 6 is provided with a treatment section 36 that has a forceps cup 36a connected to the tip end side of the insertion section 5, and a forceps operating section 37 that is connected to the bottom end side of the insertion section 5 and operates the treatment section 36. The forceps operating section (treatment tool operating section) 37 projects outward from a hole 23e along the central axis of the bobbin 25 and perpendicular to the smaller outer diameter section 25b, The treatment tool operating section 37 may be connected to the insertion section 5 via the bobbin 25.

An operating wire 38 to operate the treatment section 36 is inserted into the inside of the insertion section 5 of the biopsy forceps 6. The end section of the operating wire 38 is attached to a slider 37a of the forceps operating section 37. The slider 37a can be locked by a ratchet mechanism or a biasing mechanism such as a spring so as not to move forward towards the tip end side.

The components from which the treatment tool unit 7 is constructed are formed of a material, such as polysulfone, that is resistant to sterilization and disinfection chemicals currently in use, and to the heat of high pressure steam sterilization.

Next, the operation method of the endoscope treatment tool insertion-extraction system 1 of the present embodiment is described with reference to FIG. 6A to FIG. 10B.

Figure 7A:
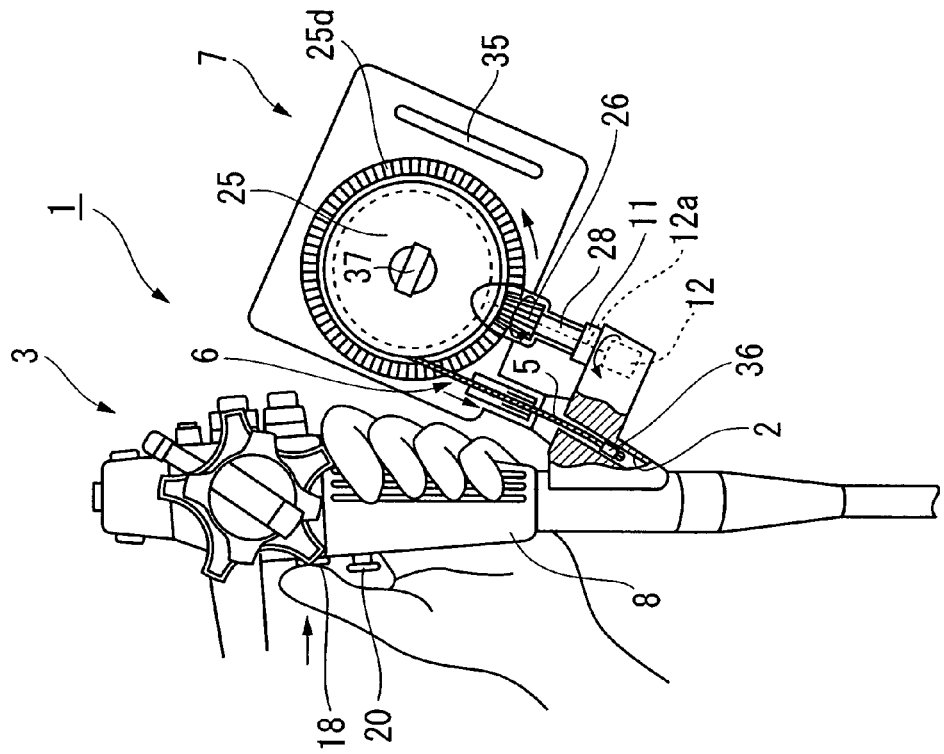
FIG. 7A and FIG. 7B are diagrams to describe an operation method of the same endoscope treatment tool insertion-extraction unit.

After the endoscope 3 is inserted in a body cavity, as shown in the FIG. 6A, the forceps opening connection member 31 of the treatment tool unit 7 is connected to the forceps opening 10, and the motor connection section 22 is joined to the connection section 11. As a result, as shown in FIG. 7A, the treatment tool unit 7 is set in the endoscope 3.

Figure 7B:
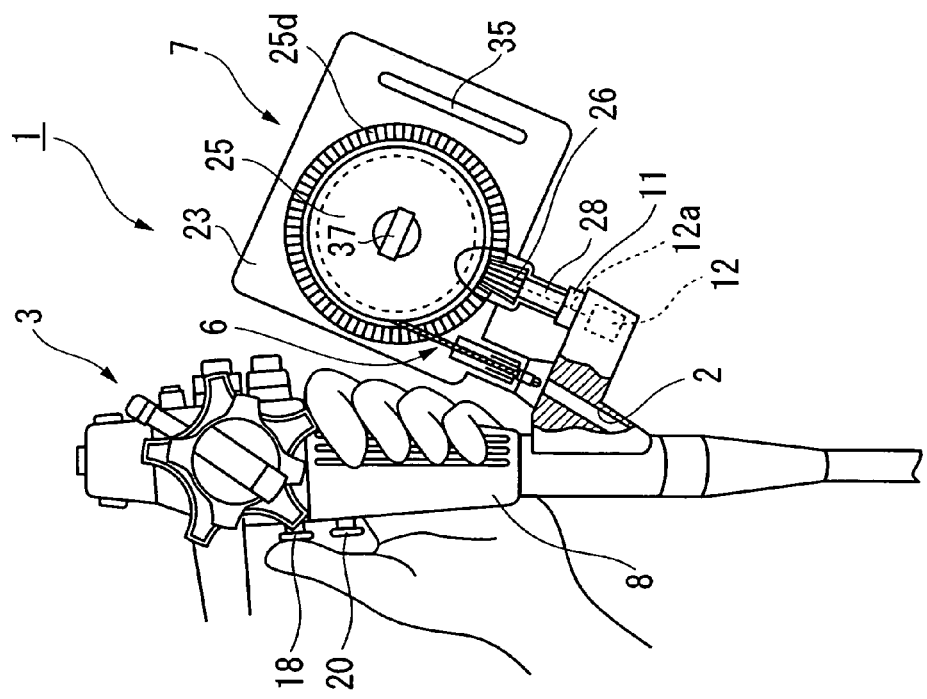

Next, as shown in FIG. 7B, when the first switch 18 of the operating section 8 is pressed, the motor 12 rotates clockwise, and the rotation force transmitted from the rotation shaft 12a to the gear 26 is transmitted to the bobbin 25 via the teeth 25d, and the bobbin 25 rotates counterclockwise. As a result, the treatment section 36 and the insertion section 5 of the biopsy forceps 6 are inserted into the forceps channel 2 from the forceps opening 10.

Then observation is carried out with the endoscope 3, and when the treatment section 36 at the tip end has reached an appropriate position, the movement of the biopsy forceps 6 is stopped by releasing the first switch 18 and stopping the rotation of the motor 12.

Figure 8:
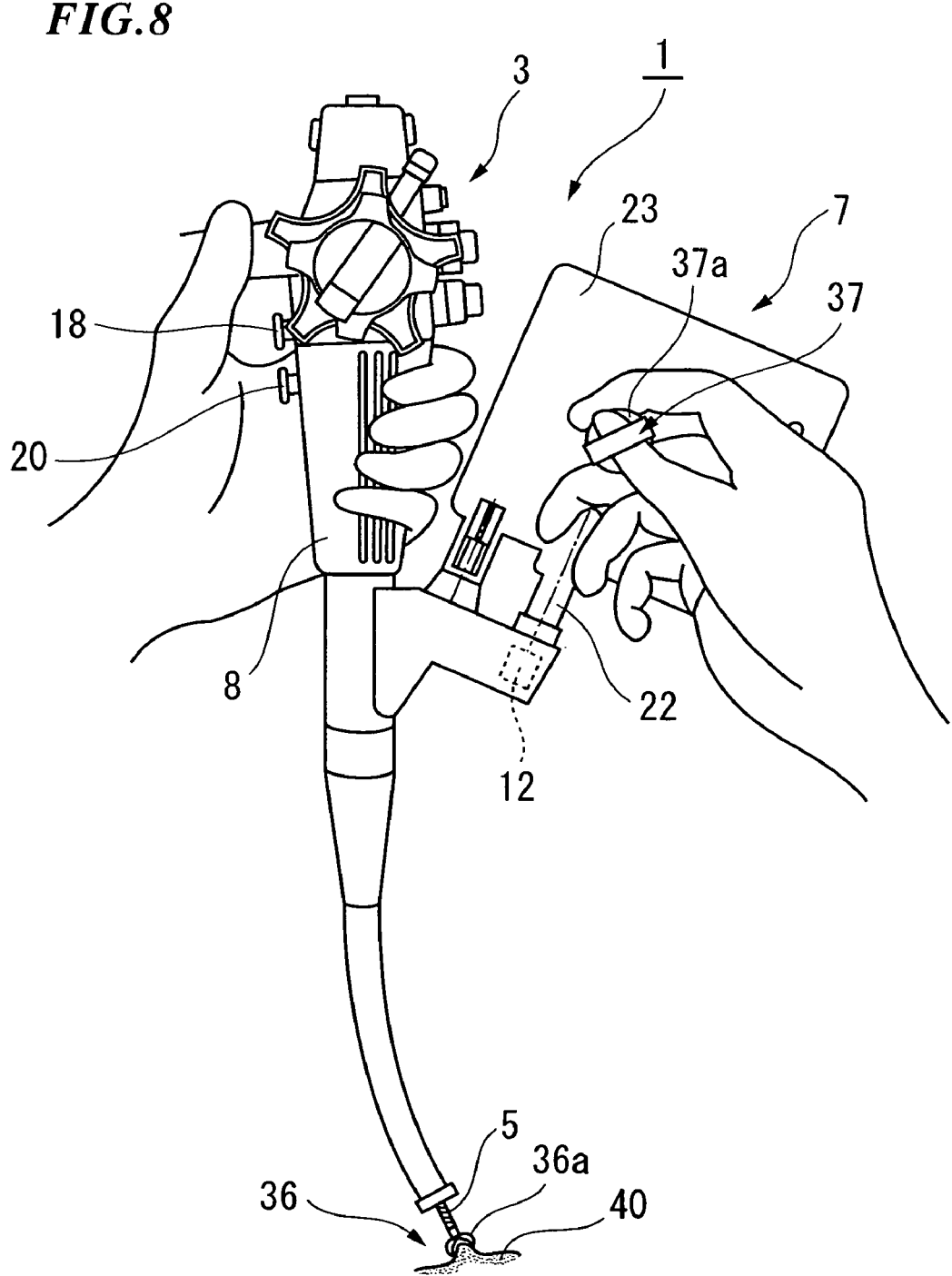
FIG. 8 is a diagram to describe the operation method of the same endoscope treatment tool insertion-extraction unit.

Subsequently, as shown in FIG. 8, the forceps cup 36a of the treatment section 36 is opened by moving the slider 37a of the forceps operating section 37 forward. Next, with the forceps cup 36a opened, the biopsy forceps 6 is pressed against the tissue 40 of the test object by pressing the first switch 18 for a moment or by slightly inserting the endoscope 3.

Then, the tissue 40 is taken into the forceps cup 36a by pulling the slider 37a towards the operator and closing the forceps cup 36a, Then, having closed the forceps cup 36a completely, as shown in FIG. 9A to FIG. 9C, the knob 33a of the holding section is gripped and the insertion section 5 of the biopsy forceps 6 is held and pulled in the lengthwise direction of the window 32. As a result, the treatment section 36 is pulled and the collection of the tissue 40 is completed.

Figure 10A:
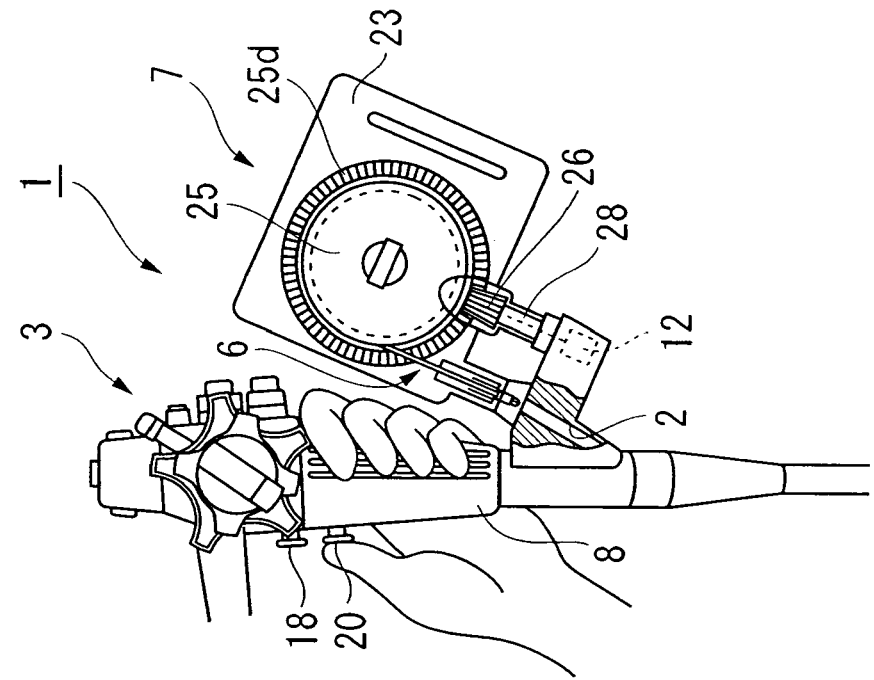
FIG. 10A and FIG. 10B are diagrams to describe the operation method of the same endoscope treatment tool insertion-extraction unit.
Figure 10B:
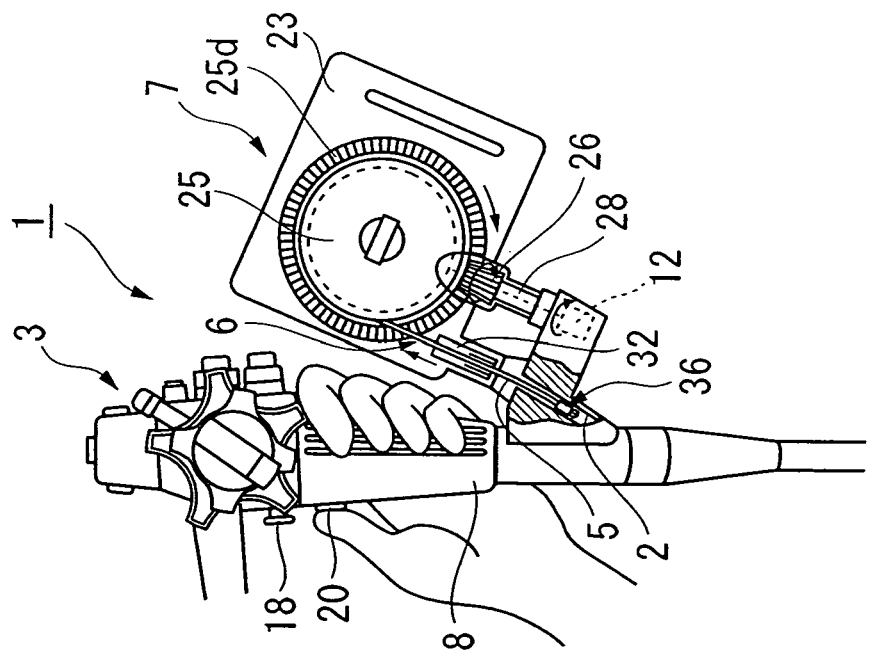

Thereafter, as shown in FIG. 10A, the insertion section 5 of the biopsy forceps 6 is rewound onto the bobbin 25 by pressing the second switch 20 and rotating the motor 12 in reverse rotation (counterclockwise rotation), rotating the bobbin 25 clockwise. Then, as shown in FIG. 10B, when extraction from the forceps channel 2 of the endoscope 3 is completed, the second switch 20 is released and the rotation of the motor 12 is stopped.

Figure 11:
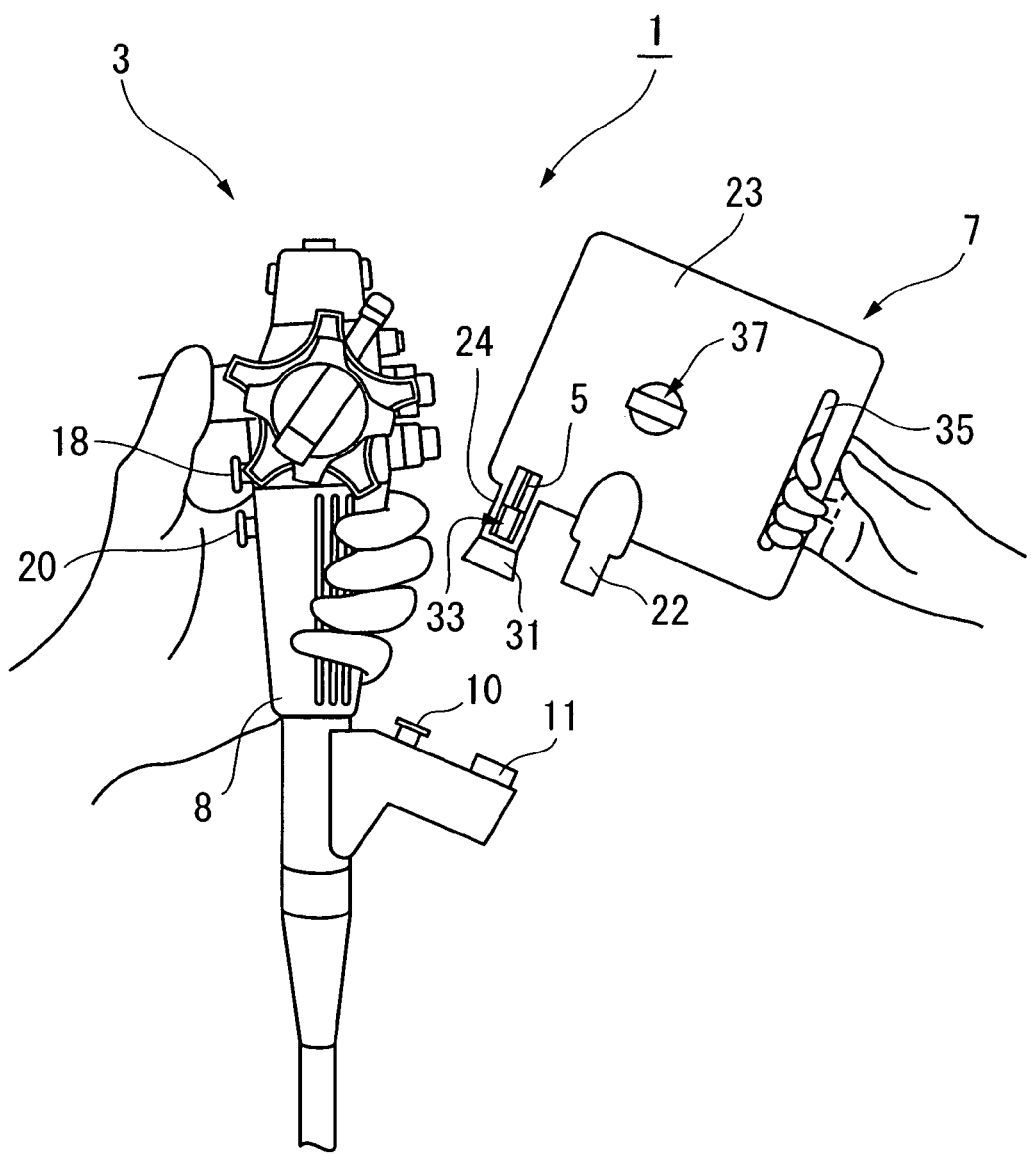
FIG. 11 is a diagram to describe the operation method of the same endoscope treatment tool insertion-extraction unit.

Thereafter, as shown in FIG. 11, the treatment tool unit 7 is detached from the endoscope 3, and the entire treatment tool unit 7 is transferred to the processing of the collected sample.

According to the endoscope treatment unit 1 of the present embodiment described above, when the biopsy forceps 6 is inserted and extracted from the forceps channel 2, the biopsy forceps 6 need not be supported by hand, and also the possibility of excessive load on the biopsy forceps 6 can be reduced. Therefore, insertion and extraction of the biopsy forceps 6 can be easily carried out.

Moreover, an operator who operates the endoscope 3 is also able to operate the biopsy forceps 6 at the same time.

Furthermore, since the treatment tool unit 7 is not provided with a driving section such as the motor 12, the treatment tool unit can be made compact and inexpensive.

Figure 12:
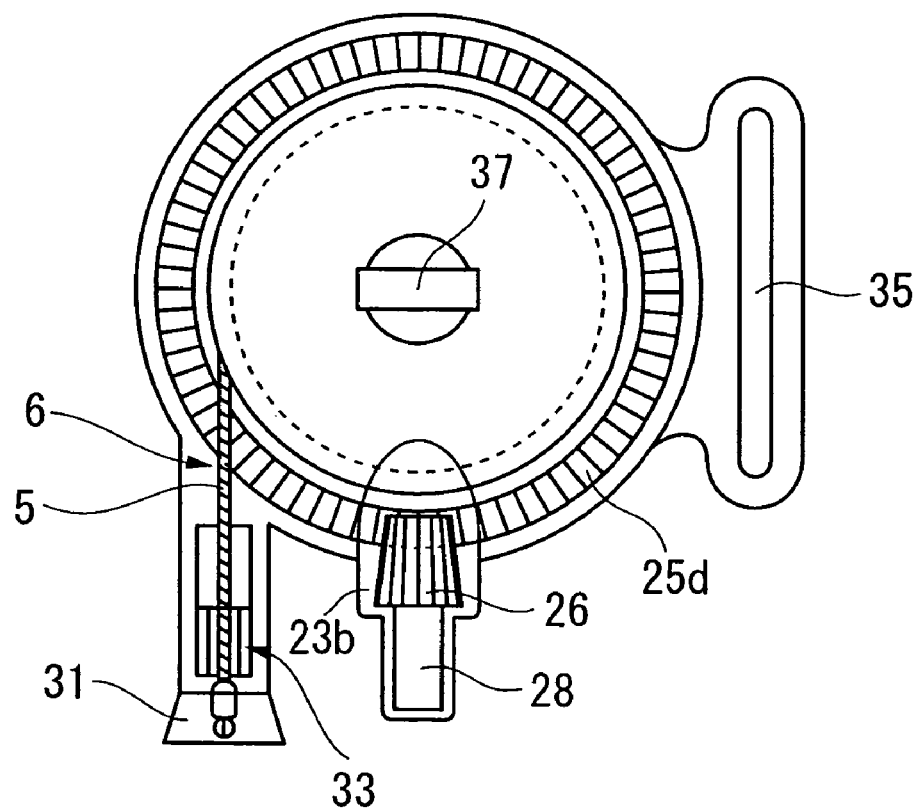
FIG. 12 is a side view showing another example of the same endoscope treatment tool insertion-extraction unit, with some parts in cross section.

Moreover, the shape of the cassette 23 is not limited to a square shape, and for example, as shown in FIG. 12, a round shape similar to the bobbin 25 may be employed.

Also, a built-in battery in the operating section 8 may be employed as the motor drive power source 16.

Next, a second embodiment of the present invention is described with reference to FIG. 13 to FIG. 18. The same reference symbols are given to the components the same as those of the first embodiment, and their descriptions are omitted.

Figure 13:
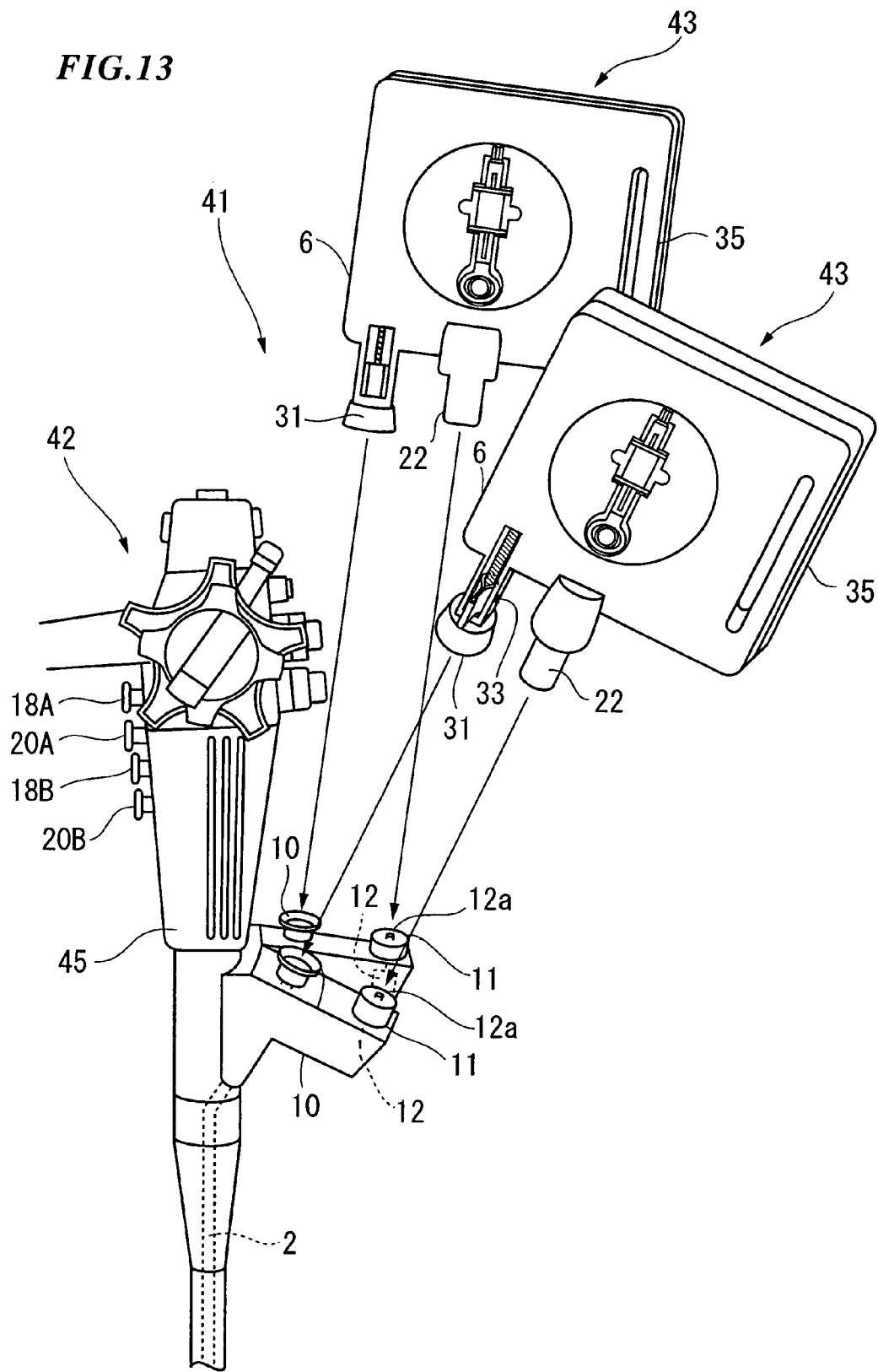
FIG. 13 is a perspective view showing an entire endoscope treatment tool insertion-extraction system according to a second embodiment of the present invention.
Figure 14B:
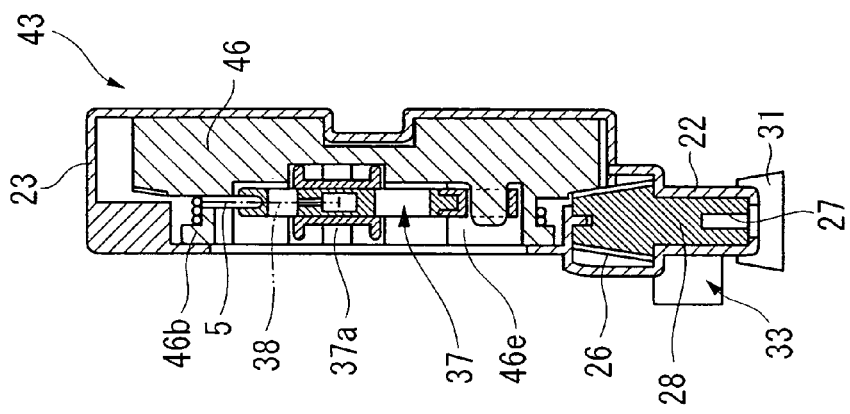
FIG. 14A and FIG. 14B are respectively a side view and a cross sectional view of the treatment tool unit of the same embodiment.
Figure 14A:
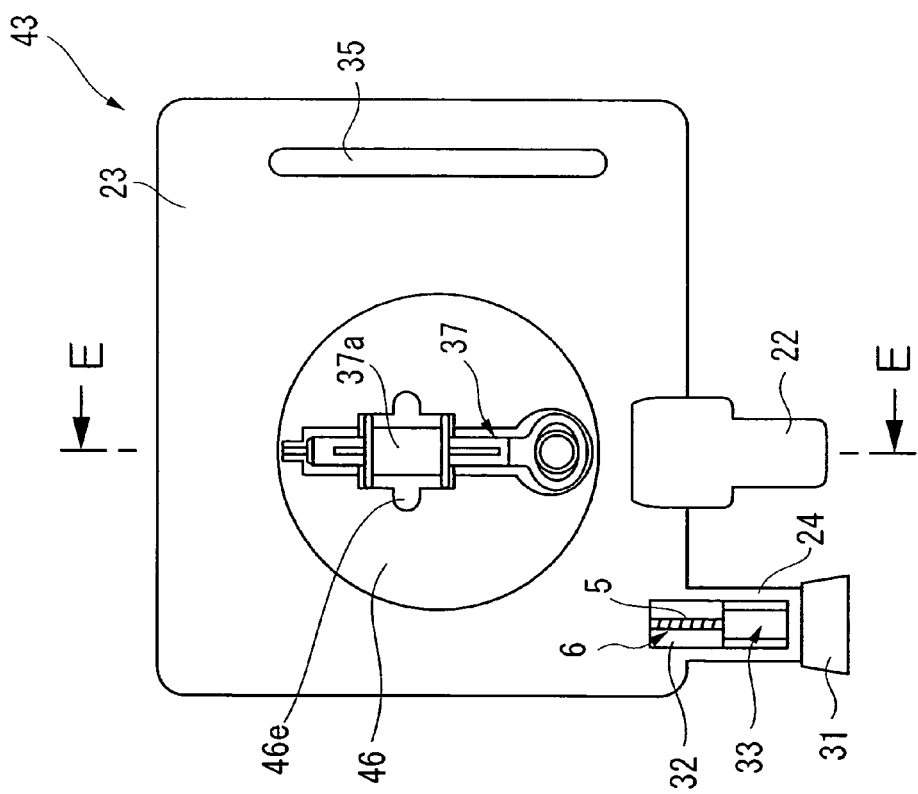
Figure 15:
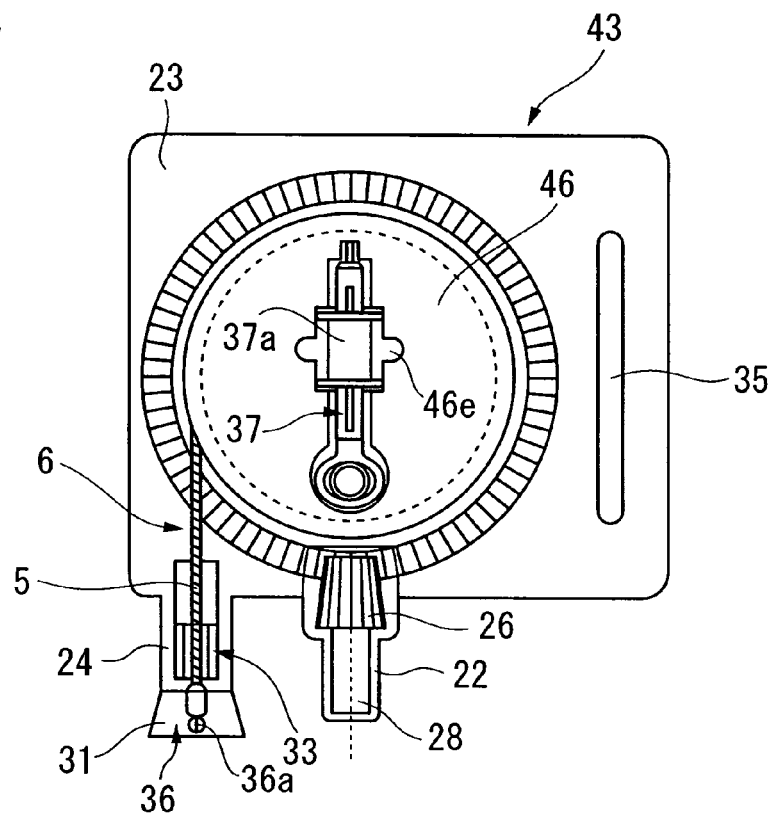
FIG. 15 is a side view of the same treatment tool unit, with some parts in cross section.

The present embodiment differs from the first embodiment mainly in that an endoscope 42 of an endoscope treatment tool insertion-extraction system 41 of the present embodiment is provided with two forceps channels 2 and two treatment tool units 43. As shown in FIG. 13, two motors 12 are respectively arranged as in the first embodiment near each forceps opening 10. First switches 18A and 18B and second switches 20A and 20B which rotate and stop each of the motors 12 are arranged on an operating section 45. As shown in FIG. 14A to FIG. 15, for each of the treatment tool units 43, the forceps operating section 37 of the biopsy forceps 6 is housed in a concave housing section 46e provided on the side face of a smaller outer diameter section 46b of a bobbin 46, so as not to project outward from the side face of the smaller outer diameter section 46b of the bobbin 46, while allowing movement in and out.

Figure 16:
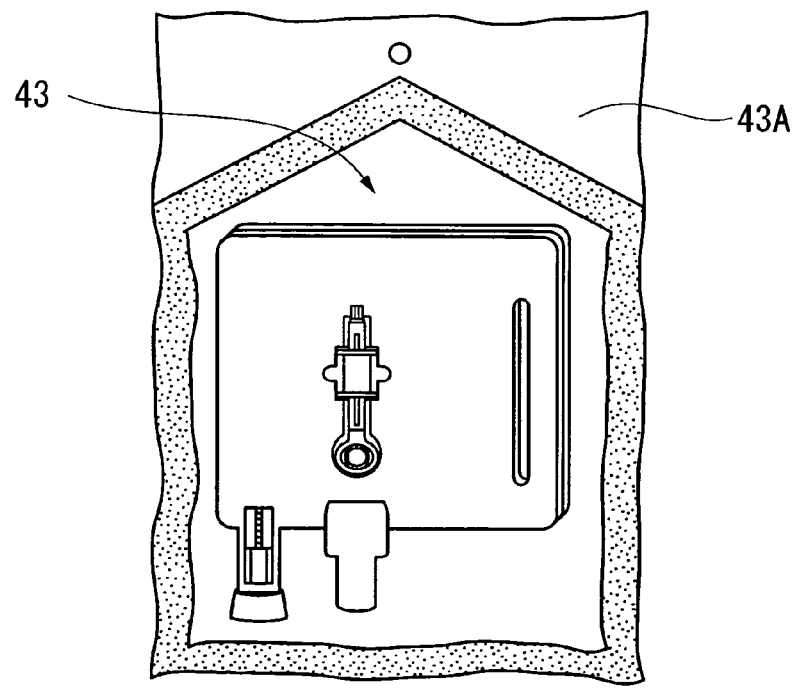
FIG. 16 is a side view of the same treatment tool unit.

As shown in FIG. 16, each of the treatment tool units 43 is pre-packaged in a sterilization bag 43A.

Figure 17:
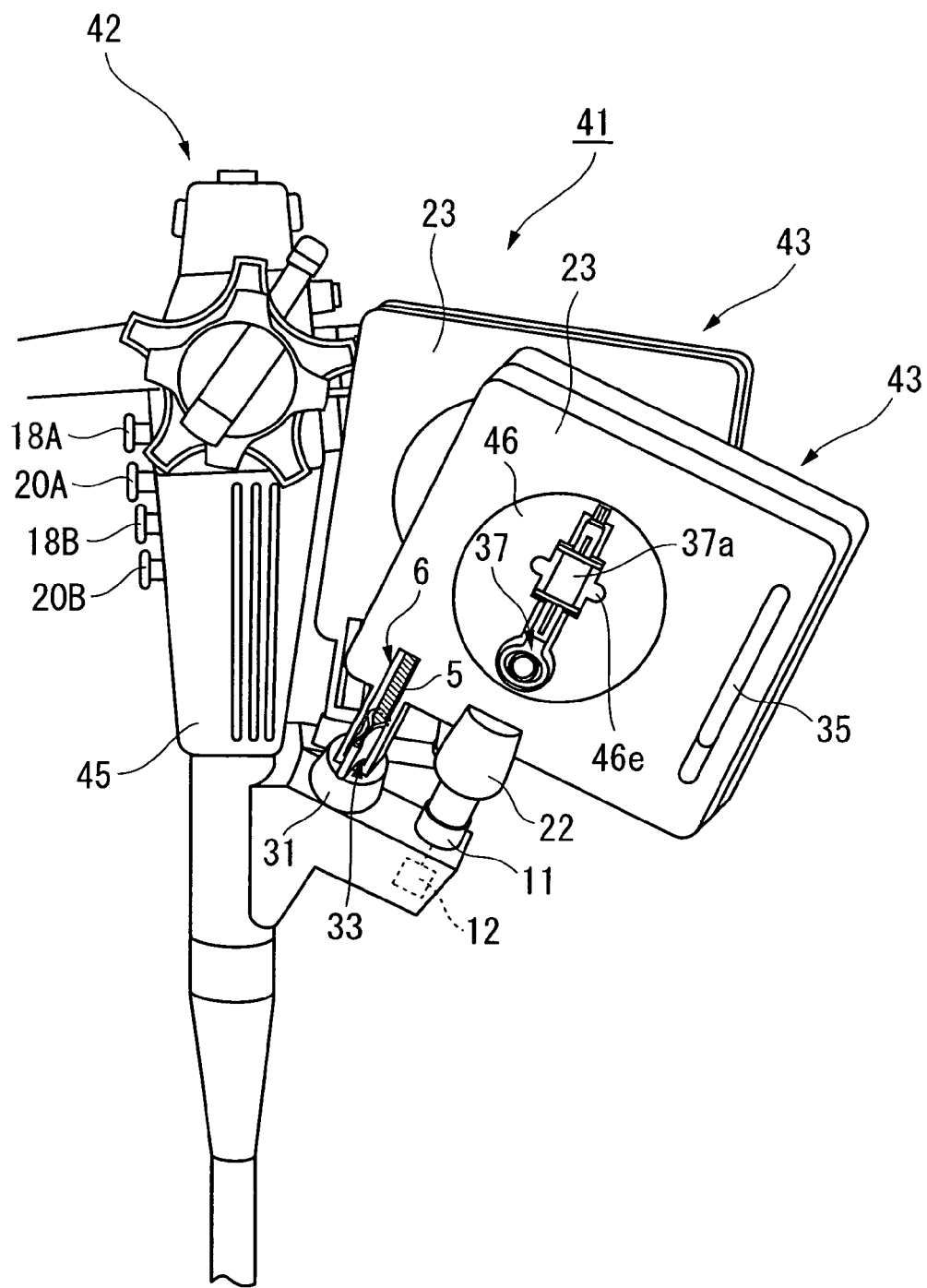
FIG. 17 is a diagram to describe an operation method of the same endoscope treatment tool insertion-extraction system.
Figure 18:
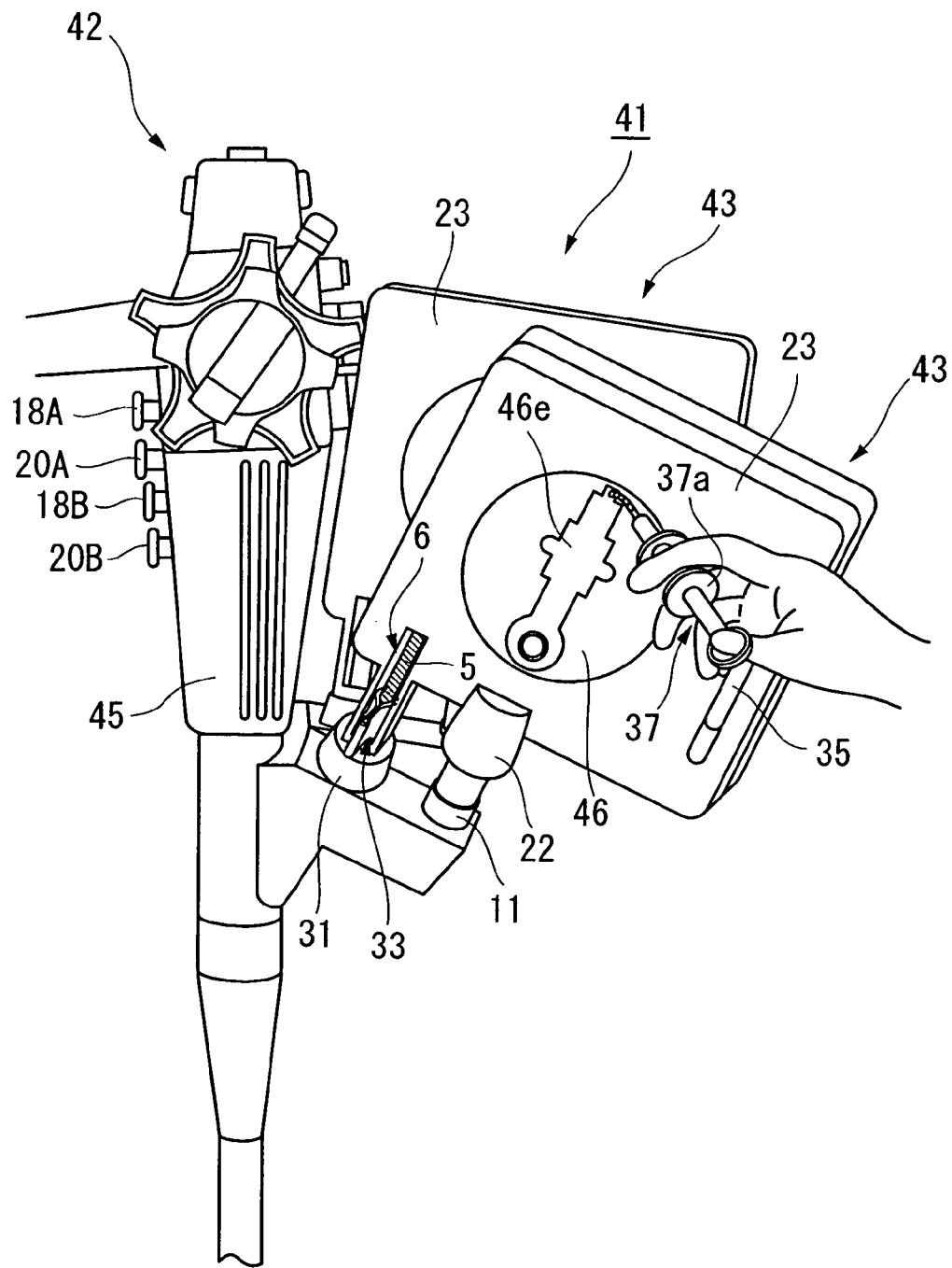
FIG. 18 is a diagram to describe the operation method of the same endoscope treatment tool insertion-extraction system.

Next, the operation method of the endoscope treatment tool insertion-extraction system 41 of the present embodiment is described with reference to FIG. 17 and FIG. 18.

First of all, each of the treatment tool units 43 is respectively attached to the endoscope 42 by a method similar to that of the first embodiment.

Then, by operating each of the first switches 18A and 18B to drive each of the motors 12, the biopsy forceps 6 of each treatment tool unit 43 is individually inserted into each forceps channel 2. When operating the treatment section 36, the forceps operating section 37 is taken out from the concave housing section 46e of the bobbin 46 and operated.

After completion of the treatment, the second switches 20A and 20B are operated and the respective insertion sections 5 are extracted from the forceps channels 2 and wound onto the bobbins 46 by an operation similar to that of the first embodiment mentioned above.

According to the endoscope treatment tool insertion-extraction system 41 of the present embodiment described above, two biopsies can be carried out in succession. Moreover, since the forceps operating section 37 is housed in the concave housing section 46e of the bobbin 46 and does not project from the cassette 23, the treatment tool units 43 that are adjacent to each other can be prevented from interfering with each other. Furthermore, storage into the sterilization bag 43A can be easily carried out.

Here, an example of a case where two biopsy forceps are used as treatment tools has been described as an example in the present embodiment, however, it is not limited to biopsy forceps, and for example, an injection needle for an endoscope and a high frequency knife may also be employed. In this case, demucosation and so forth can be carried out.

Next, a third embodiment of the present invention is described with reference to FIG. 19A to FIG. 23B. The same reference symbols are given to components the same as those of the embodiments mentioned above, and their descriptions are omitted.

Figure 19A:
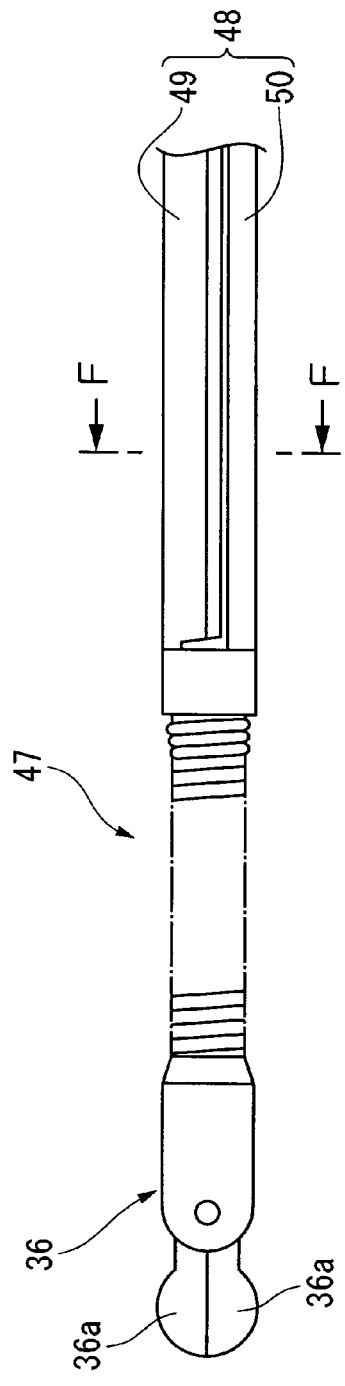
FIGS. 19A and 19B are side views of a biopsy forceps of a third embodiment of the present invention.
Figure 19B:
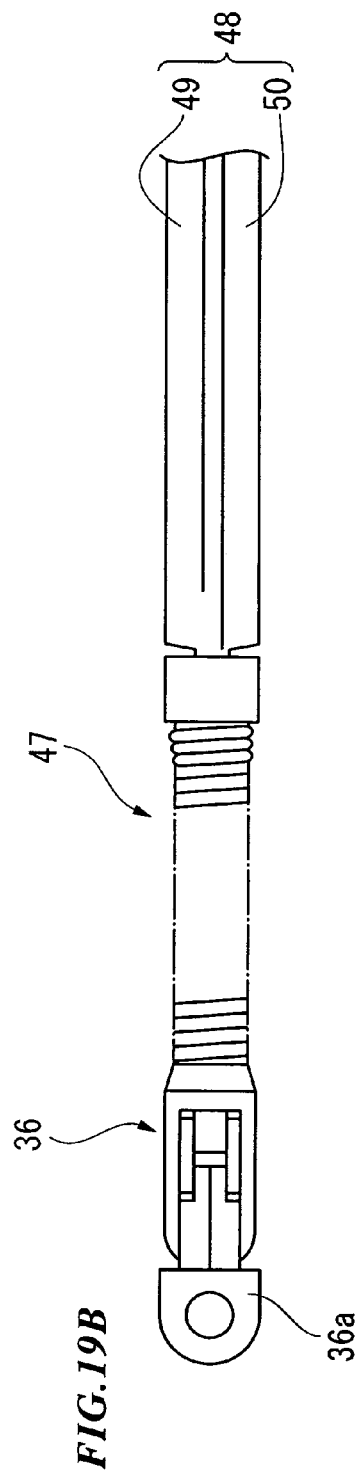
Figure 20:
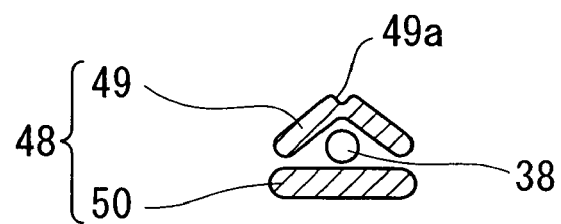
FIG. 20 is a cross sectional view along the line F-F of FIG. 19A.

The present embodiment differs from the first embodiment in that, as shown in FIG. 19A to FIG. 20, an insertion section 48 of a biopsy forceps 47 is constructed by arranging two plate shaped members 49 and 50 side by side.

On the plate shaped member 49, a folding groove 49a is formed at the widthwise center along the lengthwise direction. Moreover, this plate shaped member 49 is folded so that the folding groove 49a side faces outwards.

Figure 21:
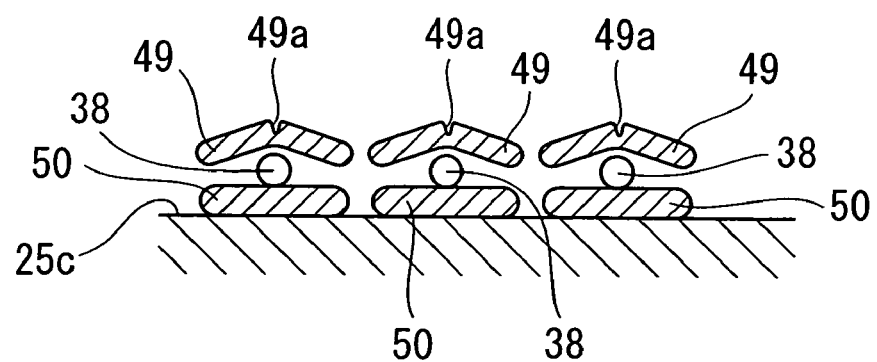
FIG. 21 is a partial sectional view showing a winding state of an insertion section of the same biopsy forceps.

When the insertion section 48 is wound onto the bobbin 25, the plate shaped member 49 expands elastically as shown in FIG. 21. When not wound, the operating wire 38 is sandwiched between the plate shaped members 49 and 50 and disposed so as not to spring out to the outside.

Figure 22:
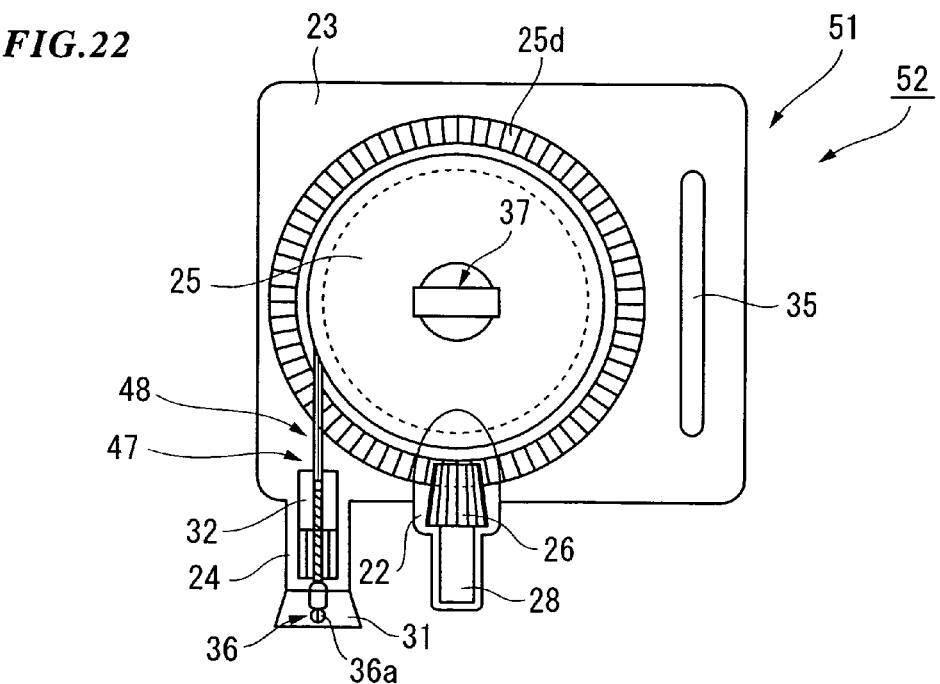
FIG. 22 is a side view of the treatment tool unit according to the same embodiment, with some parts in cross section.
Figure 23A:
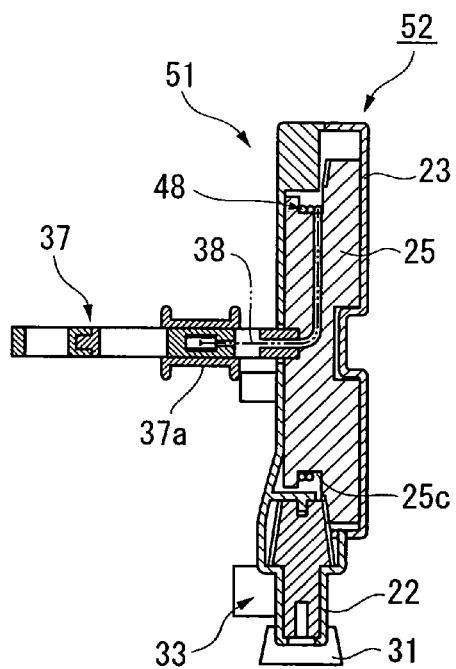
FIGS. 23A and 23B are cross sectional views of the same treatment tool unit.
Figure 23B:
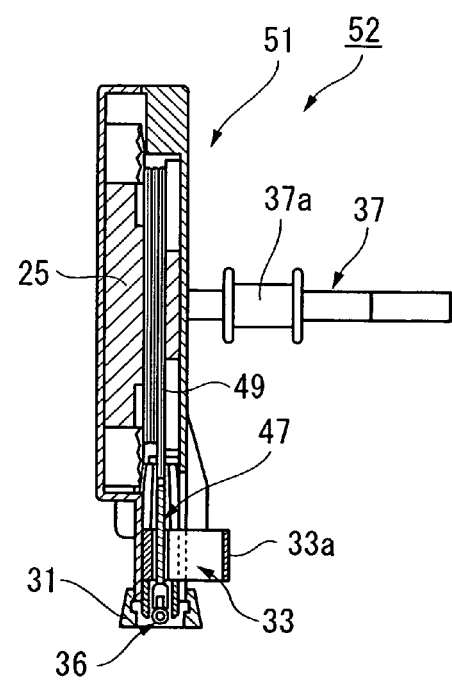
Figure 24:
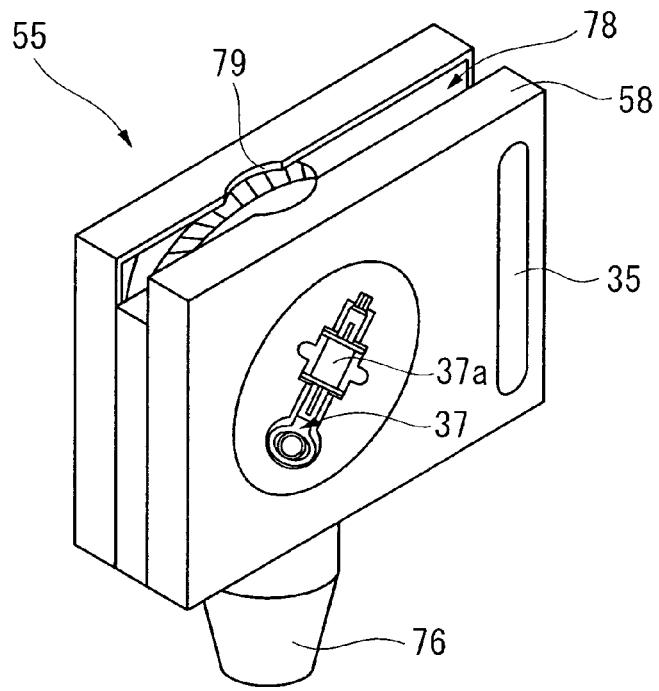
FIG. 24 is a perspective view of a treatment tool unit according to a fourth embodiment of the present invention.

The construction of the treatment tool unit 51 provided with this biopsy forceps 47 as shown in FIG. 22 to FIG. 23B is similar to that of the first embodiment except for the construction mentioned above.

According to the endoscope treatment tool insertion-extraction system 52 of the present embodiment, a function and an effect similar to that of the first embodiment can be achieved. Also, since the plate shaped members 49 and 50 can be easily bent when the insertion section 48 is wound onto the bobbin 25, easier winding can be achieved.

Next, a fourth embodiment of the present invention is described with reference to FIG. 24 to FIG. 28C. The same reference symbols are given to components the same as those of the other embodiments mentioned above, and their descriptions are omitted.

The present embodiment differs from the other embodiments in the following points.

Figure 25:
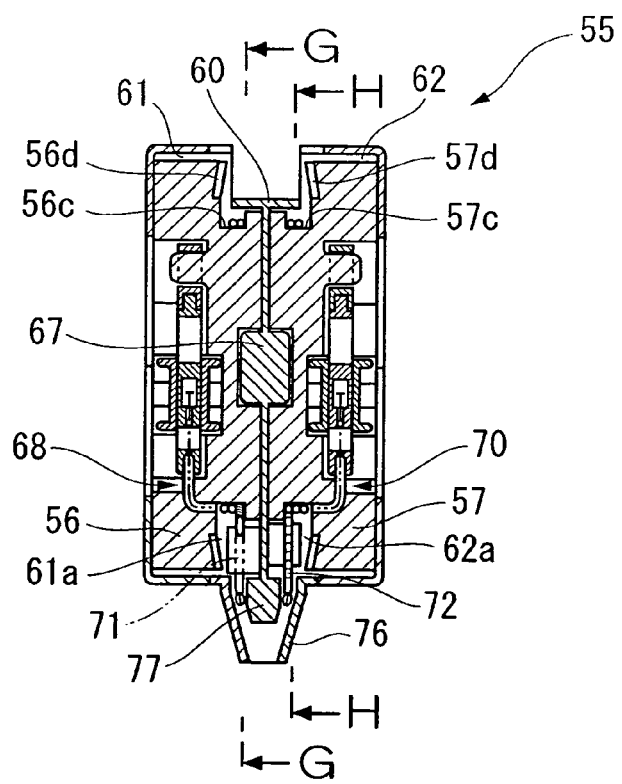
FIG. 25 is a sectional side view of the same treatment tool unit.
Figure 26A:
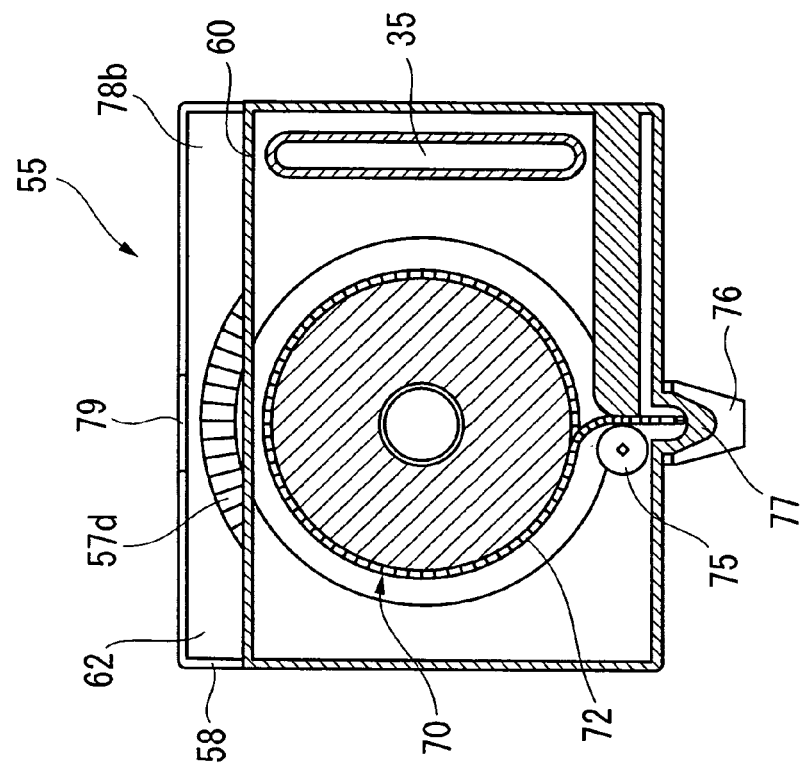
FIG. 26A and FIG. 26B are cross sectional views along the line G-G and the line H-H of FIG. 25 respectively.
Figure 26B:
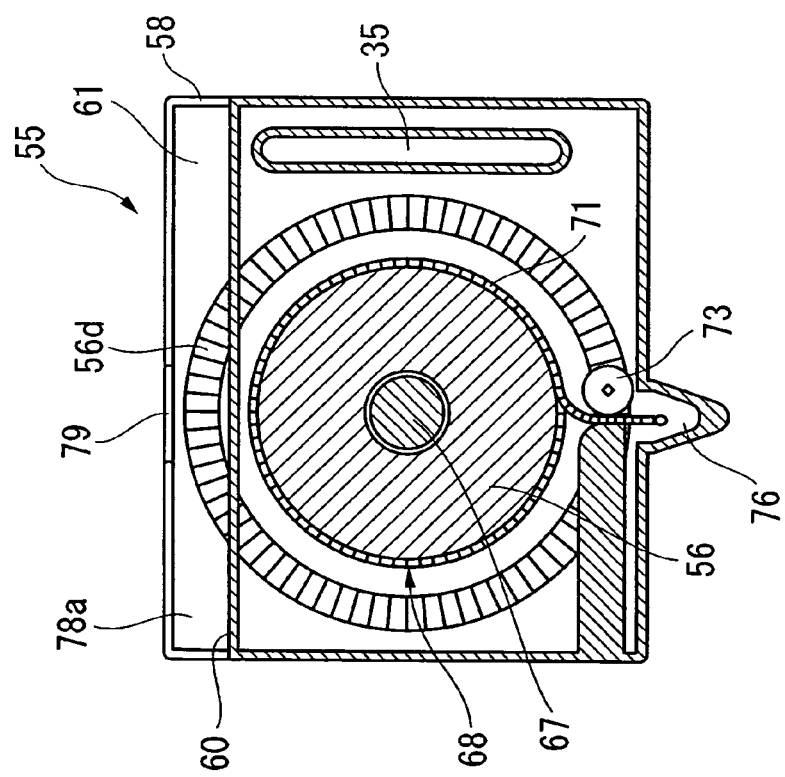

That is to say, a treatment tool unit 55 of an endoscope treatment tool insertion-extraction system 53 according to the present embodiment is provided with two bobbins 56 and 57 as shown in FIG. 24 to FIG. 26B. Two compartments 61 and 62 isolated by a partition 60 are formed in a cassette 58. As shown in FIG. 25 and FIG. 26A, the bobbins 56 and 57 are respectively rotatably supported on a protrusion 67 formed on the partition 60 so as to project towards the inside of each compartment 61 and 62.

Teeth 56d and 57d are disposed opposing each other on the circumferences of the bobbins 56 and 57. Insertion sections 71 and 72 of treatment tools 68 and 70 of the same or different kinds, are wound in opposite directions to each other onto respective winding sections 56c and 57c.

The sections near the ends of insertion sections 71 and 72 are made to face a treatment tool portal 76 that is connected to the lower part of the cassette 58 by rollers 73 and 75 rotatably provided at the lower part of the cassette 58.

A separator 77 that extends downward from the partition 60 of the cassette 58 is arranged in the treatment tool portal 76. Exits 61a and 62a of the respective compartments 61 and 62 merge at the lower part of the separator 77.

A groove 78 is formed in the upper part of the cassette 58. Faces 78a and 78b, which form a part of the groove 78, are opened so as to expose a part of the teeth 56d and 57d, Also, a motor swivel hole 79 is formed in the groove 78.

Figure 27:
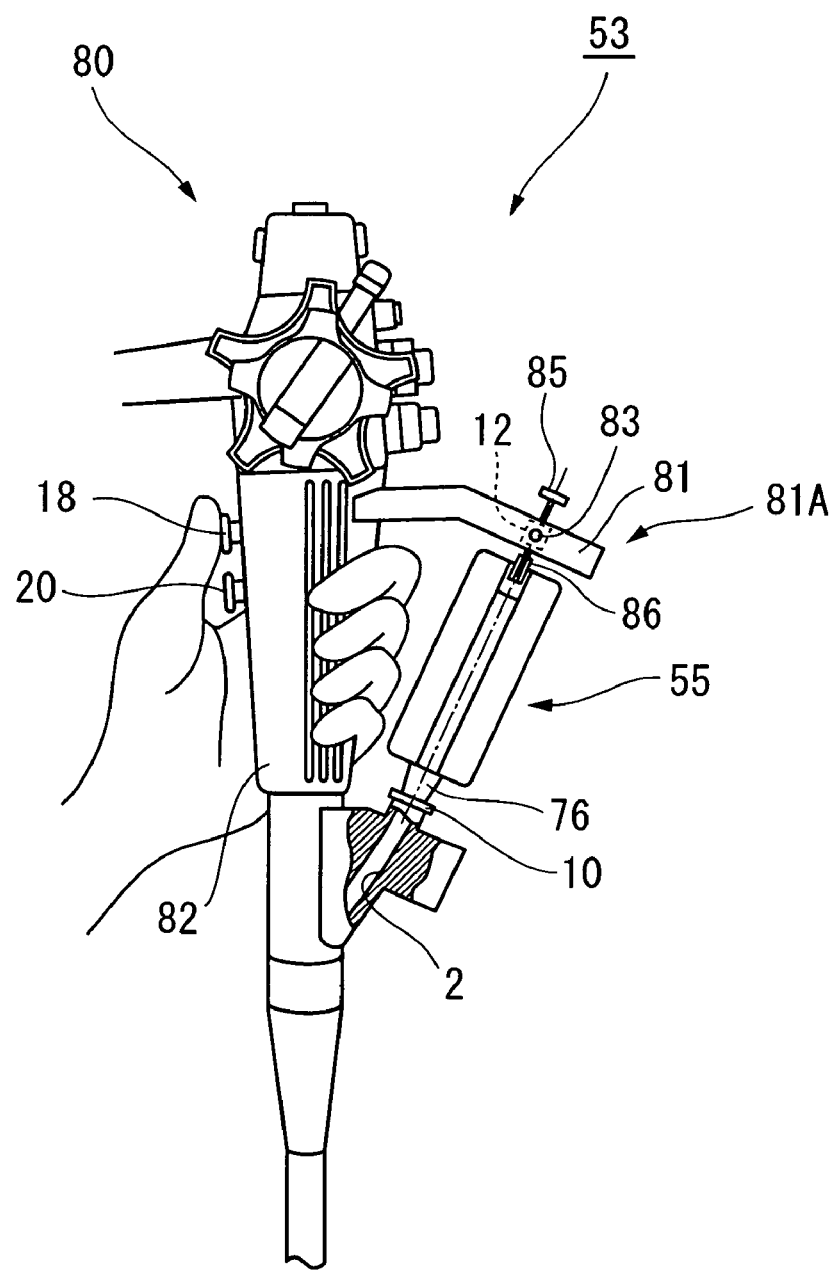
FIG. 27 is a diagram to describe an operation method of the same endoscope treatment tool insertion-extraction system.

As shown in FIG. 27, an endoscope 80 has a connection part 81 that supports a motor 12, which can be connected to the treatment tool unit 55, arranged above the forceps opening 10 and separated by a distance such that the treatment tool unit 55 can be disposed on an operating section 82.

Figure 28A:
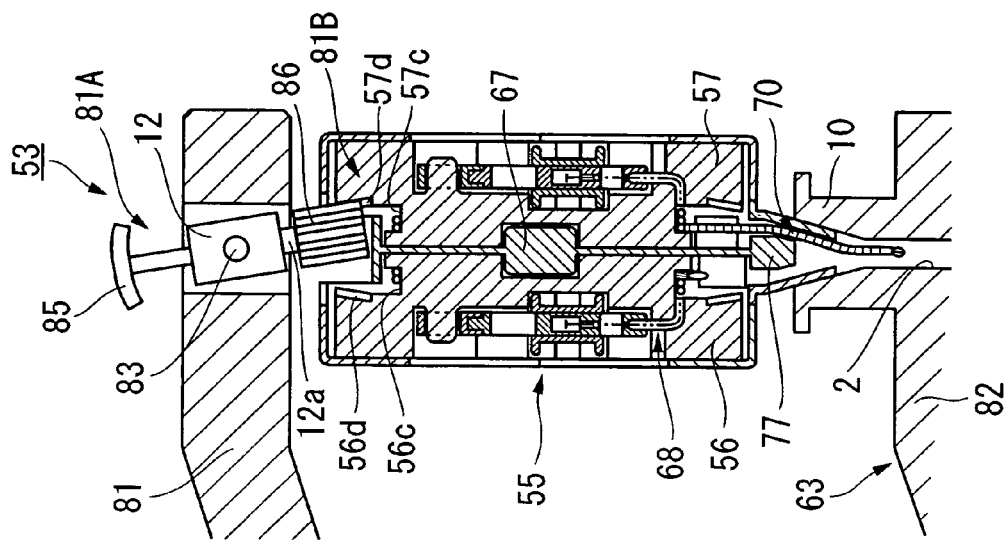
FIG. 28A to FIG. 28C are cross sectional views of the same treatment tool unit in operation.
Figure 28B:
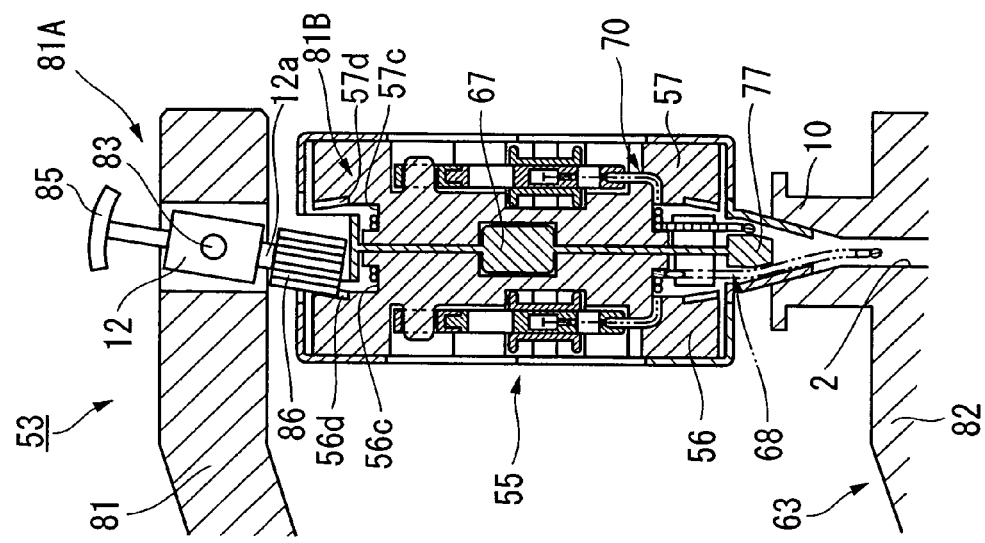
Figure 28C:
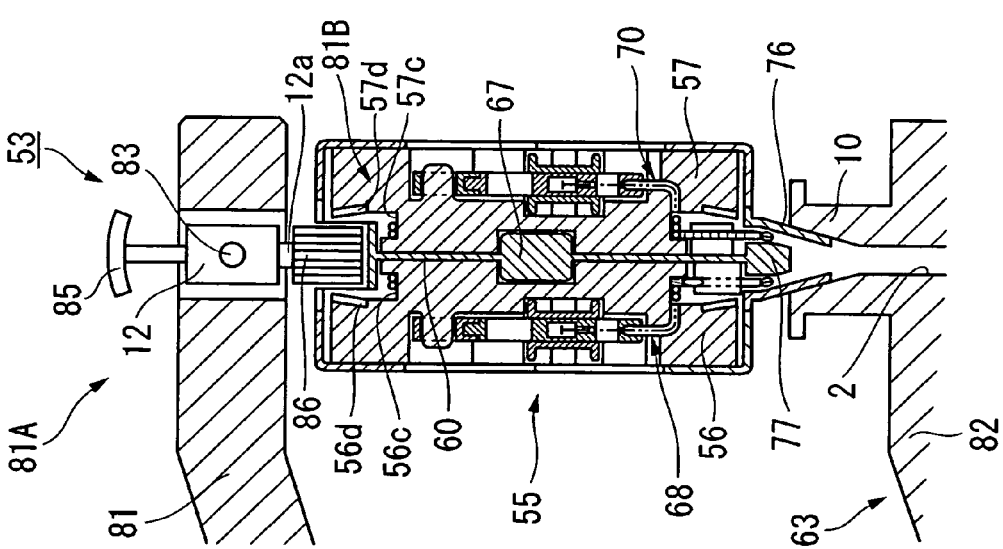

As shown in FIG. 28A to FIG. 28C, a selection mechanism 81A which selects one of either of the treatment tools 68 or 70 and inserts and extracts it, is disposed in the connection part 81. The selection mechanism 81A is provided with: the motor 12; the rotation shaft 12a of the motor 12; a pin 83 which pivots the motor 12 so as to swivel freely about the axis of the forceps opening 10; a knob 85 provided at the end part of the motor 12; and a motor gear 86, which is able to mesh with an insertion-extraction mechanism 81B having the teeth 56d and the teeth 57d, and which is provided at the end of the rotation shaft 12a of the motor 12.

Next, the operation method of the endoscope treatment tool insertion-extraction system 53 of the present embodiment is described.

After the endoscope 80 is inserted in a body cavity, the treatment tool portal 76 of the treatment tool unit 55 is attached to the forceps opening 10 as shown in FIG. 27. Furthermore, the motor gear 86 of the motor 12 is inserted into the motor swivel hole 79 of the treatment tool unit 55. In this way, the treatment tool unit 55 is attached to an endoscope 63 as shown in the FIG. 28A.

Next, as shown in FIG. 28B, firstly, when the treatment tool 68 is used, the knob 85 of the motor 12, which is the selection mechanism 81A, is inclined to the right. Then, the motor 12 swivels about the pin 83, and the motor gear 86 meshes with the teeth 56d of one bobbin 56 of the treatment tool unit 55. When the first switch 18 of the endoscope 80 is pressed, the motor 12 rotates clockwise for example, and the motor gear 86 transmits the rotation force to the teeth 56d, and the bobbin 56 rotates clockwise. As a result, the treatment tool 68 is inserted into the forceps channel 2 of the endoscope 63.

When the treatment tool 68 has reached an appropriate position while observing with the endoscope 80, by releasing the first switch 18 of the endoscope 80 and stopping the rotation of the motor 12, the movement of the treatment tool 68 is stopped. The operation method of the treatment tool 68 is similar to that of the second embodiment mentioned above.

When extracting the treatment tool 68, the motor 12 is rotated in the opposite direction (counterclockwise rotation) by pressing the second switch 20 of the endoscope 80. As a result, the bobbin 56 rotates in the opposite direction by an operation opposite to that for insertion, and the insertion section 71 of the treatment tool 68 is wound onto the bobbin 56. When the insertion section 71 is extracted from the forceps channel 2 of the endoscope 80, the second switch 20 is released and the motor 12 is stopped.

Next, the other treatment tool 70 is inserted. As shown in the FIG. 28C, when the knob 85 of the selection mechanism 81A is controlled to incline to the left, the motor 12 swivels about the pin 83, and the motor gear 86 meshes with the teeth 57d of the other bobbin 57 of the treatment tool unit 55.

Then, when the first switch 18 of the endoscope 80 is pressed, the motor 12 rotates clockwise for example, and the motor gear 86 transmits rotation force to the teeth 57d, and the bobbin 57 rotates counterclockwise. As a result, the treatment tool 70 is inserted into the forceps channel 2 of the endoscope 80.

Observing with the endoscope 80, when the treatment tool 70 has reached an appropriate position, by releasing the first switch 18 of the endoscope 80 and stopping the rotation of the motor 12, the movement of the treatment tool 70 is stopped. The operation method of the treatment tool 70 is similar to that of the second embodiment mentioned above.

The method of extracting the treatment tool 70 from the forceps channel 2 is the same as the method of extracting the treatment tool 68 from the forceps channel 2.

When the treatment tool 70 has been extracted from the forceps channel 2, the motor 12 is moved to the center, and the treatment tool unit 55 is detached from the endoscope 80.

According to the endoscope treatment tool insertion-extraction system 53 of the present embodiment described above, a function and an effect similar to that of the second embodiment can be achieved, and in addition, two treatment tools can be inserted and extracted selectively and easily through one forceps channel.

Preferable embodiments of the present invention have been described above, however, the present invention is not limited to these embodiments. Addition, omission, substitution, and other modifications to the construction within a scope which does not deviate from the gist of the present invention are also possible. The present invention is not limited by the description mentioned above, and is limited only by the scope of the appended claims.

An endoscope treatment tool insertion-extraction system of the present invention is provided with: an endoscope having a forceps channel, and a treatment tool unit having a treatment tool that can be inserted and extracted through the forceps channel; and the treatment tool unit is provided with an insertion-extraction mechanism which carries out feeding into or drawing out of the treatment tool through the forceps channel, and a driving section that drives this insertion-extraction mechanism.

According to this endoscope treatment tool insertion-extraction system, when the treatment tool is inserted and extracted through the forceps channel, it is possible to insert and extract the treatment tool without having to support it by hand. Moreover, the possibility of excessive load on the treatment tool due to manual operation can be reduced. Therefore, it becomes easy to carry out insertion and extraction of the biopsy forceps 6.

That is, by connecting the treatment tool to the endoscope, the treatment tool need no longer be supported when inserting and extracting the treatment tool, so that the treatment tool no longer gets damaged. Therefore, insertion and extraction of the treatment tool can be made easier, and it can be manufactured compactly and inexpensively. Furthermore, it becomes possible for the operator who operates the endoscope to also operate the treatment tool.

The insertion-extraction mechanism may be provided with a rotation member that winds the treatment tool, and a conversion mechanism that converts a driving force of the driving section into a rotation force of the rotation member.

In this case, the treatment tool can be compactly housed by winding it onto the rotation member. Also, inexpensive production can be achieved. Furthermore, by rotating the rotation member using the driving force of the driving section, the treatment tool wound onto the rotation member can be fed into the forceps channel, or it can be drawn back from the forceps channel to be wound onto the rotation member.

The treatment tool unit may be provided with a manual operating section whereby part of the treatment tool is manually moved forward and backward.

In this case, the control of forward and backward movement of the treatment tool can be divided as necessary, being carried out by the driving section or manually carried out. For example, when a slight forward and backward movement control of the treatment tool is required, it can be controlled manually.

Teeth may be formed on the circumference of the rotation member, and the conversion device may be a gear that meshes with the teeth.

A power source of the driving section may be built into a light source apparatus of the endoscope.

In this case, since the treatment tool unit does not need to be supported by hand when inserting and extracting the treatment tool, damage to the treatment tool can be reduced, and its insertion and extraction to the endoscope can easily be carried out. Also, the treatment tool can be compactly housed, and it can be manufactured at low cost since the construction is simple.

A power source of the driving section may be built into an operating section of the endoscope.

In this case, construction can be simplified by employing a battery or the like as the power source instead of employing a power source having a large scale circuit.

An operating section of the treatment tool may be provided on a rotation axis of the rotation member.

In this case, the operating section will not swing even when rotating, and will not be an obstruction.

An operating section of the treatment tool may be built into the rotation member, so that it can be taken out from this rotation member.

In this case, the operating section does not become obstructive.

The manual operating section may be provided with a grip part that manually grips the treatment tool.

In this case, forward and backward movement can be manually controlled by gripping the treatment tool with the grip part just when a slight forward and backward movement operation of the treatment tool is required.

A finger hole to hold this treatment tool unit by hand may be provided in the treatment tool unit.

In this case, transport of the treatment tool unit can be made easy.

The forceps channel and the treatment tool unit may be provided as two each.

In this case, two treatment tool units can be attached to the endoscope.

At least the part of the insertion section of the treatment tool that is wound onto the rotation member may be constructed of two overlapped plate shaped members, and at least one of these plate shaped members may have a folding groove provided in the widthwise center along its lengthwise direction, and be folded so that the folding groove faces outwards.

In this case, the insertion section can be made easy to wind onto the rotation member.

The treatment tool and the insertion-extraction mechanism may be provided as two each in the treatment tool unit.

Rotation members onto which each of the treatment tools is wound may be provided for each of the insertion-extraction mechanisms, and these rotation members may be connectable to the driving section.

A selection section may be provided, which selects either of the two insertion-extraction mechanisms and connects it to the driving section.

In this case, insertion and extraction of the two treatment tools can be done easily even if the endoscope has only one each of a forceps channel and a driving section.

Each of the rotation members may be disposed coaxially, and teeth which mesh with the driving section while opposing to each other, may be provided on each circumference of these rotation members, and the two insertion sections may be respectively wound in opposite directions, onto the rotation members.

In this case, the direction of the insertion and extraction of two treatment tools can be the same direction for one driving direction of the driving section.

The treatment tool unit mentioned above may be packaged in a sterile condition.

In this case, it can be directly taken out of the package, and it can be used as a disposable.

The treatment tool unit may be provided with a property of resistance to chemicals for disinfection and sterilization and to high pressure steam sterilization.

In this case, it can be reused by disinfecting and sterilizing it.

A part that projects from the rotation member of the insertion section of the treatment tool may move forward and backward along a direction tangential to the rotation member.

The driving section may be provided with a motor.

The shape of the treatment tool unit may be a substantially circular shape.

What is claimed is:

1. An endoscope treatment tool insertion-extraction system provided with an endoscope having at least one forceps channel, and at least one treatment tool unit having a treatment tool that can be inserted and extracted through said forceps channel, wherein:
    said treatment tool unit is provided with an insertion-extraction mechanism which carries out feeding into or drawing out of said treatment tool through said forceps channel, and a driving section that drives this insertion-extraction mechanism;
    said insertion-extraction mechanism is provided with a rotation member that winds said treatment tool, and a conversion mechanism that converts a driving force of said driving section into a rotation force of said rotation member, so that an axis of rotation of the driving section is non-parallel to an axis of rotation of the rotation member;
    said treatment tool is provided with an operating section on a rotation axis of said rotation member; and
    teeth are formed on the outer circumference of said rotation member, and said conversion mechanism is a gear that meshes with said teeth.

2. An endoscope treatment tool insertion-extraction system according to claim 1, wherein the operating section is a manual operating section whereby part of said treatment tool is manually moved forward and backward.

3. An endoscope treatment tool insertion-extraction system according to claim 1, wherein a power source of said driving section is built into a light source apparatus of said endoscope.

4. An endoscope treatment tool insertion-extraction system according to claim 1, wherein a power source of said driving section is built into an operating section of said endoscope.

5. An endoscope treatment tool insertion-extraction system according to claim 2, wherein said manual operating section is provided with a grip part adapted to allow a user to manually grip said treatment tool.

6. An endoscope treatment tool insertion-extraction system according to claim 1, wherein a finger hole to hold this treatment tool unit by hand is provided in said treatment tool unit.

7. An endoscope treatment tool insertion-extraction system according to claim 1, wherein a pair of said forceps channels and a pair of said treatment tool units are provided.

8. An endoscope treatment tool insertion-extraction system according to claim 1, wherein:
    the treatment tool includes an insertion section;
    at least a part of the insertion section of said treatment tool that is wound onto said rotation member is constructed of two overlapped plate shaped members; and
    at least one of these plate shaped members has a folding groove provided in the widthwise center along its lengthwise direction, and is folded so that said folding groove faces outwards.

9. An endoscope treatment tool insertion-extraction system according to claim 1, wherein said treatment tool unit is packaged in a sterile condition.

10. An endoscope treatment tool insertion-extraction system according to claim 1, wherein said treatment tool unit is provided with a property of resistance to chemicals for disinfection and sterilization and to high pressure steam sterilization.

11. An endoscope treatment tool insertion-extraction system according to claim 1, wherein:
    the treatment tool includes an insertion section; and
    a part of the insertion section of said treatment tool that projects from said rotation member moves forward and backward along a direction tangential to said rotation member.

12. An endoscope treatment tool insertion-extraction system according to claim 1, wherein said driving section is provided with a motor.

13. An endoscope treatment tool insertion-extraction system provided wish an endoscope having at least one forceps channel, and at least one treatment tool unit having a treatment tool that can be inserted and extracted through said forceps channel, wherein:
    said treatment tool unit is provided with an insertion-extraction mechanism which carries out feeding into or drawing out of said treatment tool through said forceps channel, and a driving section that drives this insertion-extraction mechanism;
    said insertion-extraction mechanism is provided with a rotation member that winds said treatment tool, and a conversion mechanism that converts a driving force of said driving section into a rotation force of said rotation member, so that an axis of rotation of the driving section is non-parallel to an axis of rotation of the rotation member;
    said treatment tool is provided with an operating section built into said rotation member, so as to be removable from the rotation member; and
    teeth are formed on the outer circumference of said rotation member, and said conversion mechanism is a gear that meshes with said teeth.

14. An endoscope treatment tool insertion-extraction system according to claim 13, wherein the operating section is a manual operating section whereby part of said treatment tool is manually moved forward and backward.

15. An endoscope treatment tool insertion-extraction system according to claim 13, wherein a power source of said driving section is built into a light source apparatus of said endoscope.

16. An endoscope treatment tool insertion-extraction system according to claim 13, wherein a power source of said driving section is built into an operating section of said endoscope.

17. An endoscope treatment tool insertion-extraction system according to claim 14, wherein said manual operating section is provided with a grip part adapted to allow a user to manually grip said treatment tool.

18. An endoscope treatment tool insertion-extraction system according to claim 13, wherein a finger hole to hold this treatment tool unit by hand is provided in said treatment tool unit.

19. An endoscope treatment tool insertion-extraction system according to claim 13, wherein a pair of said forceps channels and a pair of said treatment tool units are provided.

20. An endoscope treatment tool insertion-extraction system according to claim 13, wherein:

the treatment tool includes an insertion section;

at least a part of the insertion section of said treatment tool that is wound onto said rotation member is constructed of two overlapped plate shaped members; and at least one of these plate shaped members has a folding groove provided in the widthwise center along its lengthwise direction, and is folded so that said folding groove faces outwards.

21. An endoscope treatment tool insertion-extraction system according to claim 13, wherein said treatment tool unit is packaged in a sterile condition.

22. An endoscope treatment tool insertion-extraction system according to claim 13, wherein said treatment tool unit is provided with a property of resistance to chemicals for disinfection and sterilization and to high pressure steam sterilization.

23. An endoscope treatment tool insertion-extraction system according to claim 13, wherein:

the treatment tool includes an insertion section; and a part of the insertion section of said treatment tool that projects from said rotation member moves forward and backward along a direction tangential to said rotation member.

24. An endoscope treatment tool insertion-extraction system according to claim 13, wherein said driving section is provided with a motor.

* * * * *